(12) United States Patent
Bossenmaier et al.

(10) Patent No.: US 7,205,326 B2
(45) Date of Patent: Apr. 17, 2007

(54) ANILINE DERIVATIVES, THEIR MANUFACTURE AND USE AS PHARMACEUTICAL AGENTS

(75) Inventors: Birgit Bossenmaier, Seefeld (DE); Walter-Gunar Friebe, Mannheim (DE); Ulrike Reiff, Penzberg (DE); Matthias Rueth, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 525 days.

(21) Appl. No.: 10/833,721

(22) Filed: Apr. 28, 2004

(65) Prior Publication Data

US 2004/0254217 A1 Dec. 16, 2004

(30) Foreign Application Priority Data

Apr. 30, 2003 (EP) .................... 03009908

(51) Int. Cl.
  *A61K 31/422* (2006.01)
  *C07D 263/30* (2006.01)
  *C07D 413/02* (2006.01)

(52) U.S. Cl. ............... 514/374; 548/215; 548/235

(58) Field of Classification Search ......... 548/215, 548/235; 514/374
  See application file for complete search history.

(56) References Cited

U.S. PATENT DOCUMENTS 6,211,215 B1  4/2001  Momose et al.

2002/0173526 A1  11/2002  Tasaka et al.

FOREIGN PATENT DOCUMENTS

| EP | 1 270 571 | 1/2003 |
|---|---|---|
| WO | WO 98/03505 | 1/1998 |
| WO | WO 01/77107 | 10/2001 |

OTHER PUBLICATIONS

Baselga et al., Oncology, 63, pp. 6-16 (2002).
Chan et al., Curr. Opin. Immunol., 8, pp. 394-401 (1995).
Wilks, A. F., Progress in Growth Factor Research, 2, pp. 97-111 (1990).
Wright et al., Br. J. Cancer, 65, pp. 118-121 (1992).

*Primary Examiner*—Golam M. M. Shameem
(74) *Attorney, Agent, or Firm*—George W. Johnston; Patricia S. Rocha-Tramaloni; Brian C. Remy

(57) ABSTRACT

Compounds of formula (I)

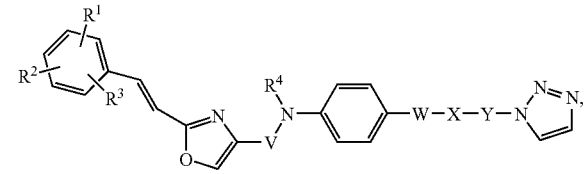

formula (I)

are useful in the therapy and/or prevention of illnesses with known over-expression of receptor tyrosine kinases of the HER-family like HER-2 and EGFR (HER-1). Accordingly, these compounds are useful for the treatment of diseases such as cancer in humans or animals.

25 Claims, No Drawings

ANILINE DERIVATIVES, THEIR MANUFACTURE AND USE AS PHARMACEUTICAL AGENTS

BACKGROUND OF THE INVENTION

The present invention relates to novel aniline derivatives, to a process for their manufacture, pharmaceutical compositions containing them and their manufacture as well as the use of these compounds as pharmaceutically active agents.

Protein tyrosine kinases (PTKs) catalyse the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394–401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443–478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER-1) are frequently aberrantly expressed in common human cancers such as breast cancer, gastrointestinal cancer such as colon, rectal or stomach cancer, leukemia and ovarian, bronchial and pancreatic cancer. High levels of these receptors correlate with poor prognosis and response to treatment (Wright, C., et al., Br. J. Cancer 65 (1992) 118–121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6–16; Sliwkowski et al., Oncology 63 (suppl. 1) (2002) 17).

Some substituted anilines are known in the art. WO 98/03505, EP 1270571 and WO 01/77107 disclose related heterocyclic compounds as tyrosine kinase inhibitors. However there remains a need for new compounds with improved therapeutic properties, such as improved activity, solubility, tolerability, selectivity or stability to name only a few.

SUMMARY OF THE INVENTION

The present invention relates to new compounds of the general formula (I), formula (I)

wherein $R^1$, $R^2$, $R^3$ and $R^4$ are as described herewithin.

The compounds of the present invention show activity as inhibitors of the HER-signalling pathway and therefore possess anti-proliferative activity. Compounds of formula (I) and their pharmaceutically acceptable salts, enantiomeric forms, diastereoisomers and racemates, are provided as an exemplary embodiment of the present invention. Other embodiments of the present invention include the preparation of the above-mentioned compounds, pharmaceutical compositions containing them and their manufacture as well as the use of the above-mentioned compounds in the control or prevention of illnesses, especially of illnesses and disorders as mentioned above or in the manufacture of corresponding medicaments.

The compounds of the present invention are useful in the therapy and/or prevention of illnesses with known over-expression of receptor tyrosine kinases of the HER-family like HER-2 and EGFR (HER-1). Accordingly, these compounds are useful for the treatment of diseases such as cancer in humans or animals. Examples of tumors which may be treated, but are not limited to, colon cancers, breast carcinoma (including advanced breast cancer), lung cancer (e.g. adenocarcinoma and including non-small cell lung cancer), prostate cancer including advanced disease, pancreatic cancers, hematopoetic tumors of lymphoid lineage (e.g. acute lymphotic leukemia, B-cell lymphoma, Burkitt's lymphoma), myeloid leukemias (for example, acute myelogenous leukemia (AML)), thyroid follicular cancer, myelodysplastic syndrome (MSD), tumors of mesenchymal origin, melanomas, teratocarcinomas, neuroblastomas, gliomas, benign tumors of the skin (e.g. keratoacanthomas), kidney carcinoma, ovary carcinoma, bladder carcinoma and epidermal carcinoma.

DETAILED DESCRIPTION OF THE INVENTION

The present invention relates to new compounds of the general formula (I), formula (I)

wherein
$R^1$ is halogen;
—O-alkyl;
—S-alkyl; —S(O)-alkyl; —S(O)$_2$-alkyl
—N-alkyl; or
alkyl, all alkyl groups being optionally once or several times substituted with halogen; and
$R^2$ is hydrogen; or
halogen; or alternatively
$R^1$ and $R^2$ together with the carbon atoms to which they are attached form a 5 or 6 membered heterocyclic ring; and
$R^3$ is hydrogen; or
halogen, provided that when $R^1$ and $R^2$ together with the carbon atoms to which they are attached do not form a 5 or 6 member heterocyclic ring, $R^3$ is hydrogen;
$R^4$ is hydrogen; or
alkyl;

V is —CH$_2$—; or
—C(O)—;
W is —CH$_2$—; or
a direct bond;
X is —NH—, —O—, —S—, —S(O)—, —S(O)$_2$—, —C(O)—, —C(O)NH—, —NHC(O)—, —S(O)$_2$NH—, —CH═CH—, or —CH$_2$—;
Y is —(CH$_2$)$_n$—; and
n is 1, 2 or 3;

or their pharmaceutically acceptable salts.

The following definitions of the general terms used in the present description apply irrespective of whether the terms in question appear alone or in combination.

The term "substituted", as in alkyl is "substituted by", means that, unless otherwise indicated, the substitution can occur at one or more positions and that the substituents at each substitution site are independently selected from the specified options.

As used herein, the term "alkyl" means a saturated, straight-chain or branched-chain hydrocarbon containing from 1 to 4, preferably 1 or 2, carbon atoms, such as methyl, ethyl, n-propyl, isopropyl, n-butyl, 2-butyl, t-butyl. Said alkyl group is optionally substituted with one or several halogen atoms, preferably fluorine. Examples are difluoromethyl, trifluoromethyl, 2,2,2-trifluoroethyl, perfluorethyl and the like.

The term "halogen" as used herein denotes fluorine, chlorine, bromine and iodine, preferably fluorine.

A "5 or 6 membered heterocyclic ring" as used herein means a monocydic saturated or unsaturated hydrocarbon with 5 or 6 ring atoms of which 1 or 2 atoms are replaced by heteroatoms selected from S, N or O, preferably from N or O, and the remaining carbon-atoms, where possible, being optionally once or several times substituted with halogen, preferably fluorine. Preferably said "5 or 6 membered heterocyclic ring" is formed by R$^1$ and R$^2$ being located on two adjacent carbon-atoms of the phenyl ring to which they are attached. Examples of a "5 or 6 membered heterocyclic ring", including the phenyl ring to which it is attached, are benzo[1,3]dioxole, 2,2-difluoro-benzo[1,3]dioxole, 1H-benzoimidazole, 2,3-dihydro-benzo[1,4]dioxine, 3,4-dihydro-2H-benzo [1,4]oxazine and the like.

The term "effective amount" or "therapeutically effective amount" means an amount of at least one compound of formula I, or a pharmaceutically acceptable salt thereof, that significantly inhibits proliferation and/or prevents differentiation of a human tumor cell, including human tumor cell lines.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and quaternary ammonium hydroxides, such as for example, tetramethylammonium hydroxide. The chemical modification of a pharmaceutical compound (i.e. a drug) into a salt is a technique well known to pharmaceutical chemists to obtain improved physical and chemical stability, hygroscopicity, flowability and solubility of compounds. See, e.g., Ansel, H., et. al., Pharmaceutical Dosage Forms and Drug Delivery Systems, 6th ed., 1995, at pp. 196 and 1456–1457.

Preferred substituents in R$^1$ are methoxy, difluoromethoxy, trifluoromethoxy, trifluoromethylsulfanyl, chloro, fluoro and trifluoromethyl.

Preferred examples for the group —W—X—Y— are:
—(CH$_2$)$_4$—; —O—(CH$_2$)$_3$—; —C(O)—(CH$_2$)$_3$—; —S—(CH$_2$)$_3$—; —S(O)$_2$—(CH$_2$)$_3$—; —S(O)—(CH$_2$)$_3$—; —S(O)$_2$—NH—(CH$_2$)$_2$—; —NH—C(O)— (CH$_2$)$_2$—; —C(O)—NH—(CH$_2$)$_2$—; —CH$_2$—NH—(CH$_2$)$_2$—; —CH═CH—CH$_2$—; —CH═CH—(CH$_2$)$_2$—; or —CH$_2$—CH═CH—CH$_2$—;.

An embodiment of the invention are the compounds of formula (I), wherein
R$^1$ is halogen;
—O-alkyl;
—S-alkyl; or
alkyl, all alkyl groups being optionally once or several times substituted with halogen; and
R$^2$, R$^3$ are both hydrogen; and
R$^4$ is hydrogen; or
methyl;
V is —CH$_2$—; and
—W—X—Y— is —(CH$_2$)$_4$—;

or their pharmaceutically acceptable salts.
Such compounds are for example:
[4-(4-[1,2,3]Triazol-1-yl-butyl)-phenyl]-{2-[2-(4-trifluoromethoxy-phenyl)-vinyl]-oxazol-4-ylmethyl}-amine;
[4-(4-[1,2,3]Triazol-1-yl-butyl)-phenyl]-{2-[2-(4-trifluoromethyl-phenyl)-vinyl]-oxazol-4-ylmethyl}-amine;
Methyl-[4-(4-[1,2,3]triazol-1-yl-butyl)-phenyl]-{2-[2-(4-trifluoromethyl-phenyl)-vinyl]-oxazol-4-ylmethyl}-amine;
{2-[2-(4-Difluoromethoxy-phenyl)-vinyl]-oxazol-4-ylmethyl}-[4-(4-[1,2,3]triazol-1-yl-butyl)-phenyl]-amine;
{2-[2-(4-Chloro-phenyl)-vinyl]-oxazol-4-ylmethyl}-[4-(4-[1,2,3]triazol-1-yl-butyl)-phenyl]-amine;
[4-(4-[1,2,3]Triazol-1-yl-butyl)-phenyl]-{2-[2-(4-trifluoromethylsulfanyl-phenyl)-vinyl]-oxazol-4-ylmethyl}-amine;
Methyl-[4-(4-[1,2,3]triazol-1-yl-butyl)-phenyl]-{2-[2-(4-trifluoromethylsulfanyl-phenyl)-vinyl]-oxazol-4-ylmethyl}-amine;
{2-[2-(4-Chloro-phenyl)-vinyl]-oxazol-4-ylmethyl}-methyl-[4-(4-[1,2,3]triazol-1-yl-butyl)-phenyl]-amine;
[4-(4-[1,2,3]Triazol-1-yl-butyl)-phenyl]-{2-[2-(3-trifluoromethyl-phenyl)-vinyl]-oxazol-4-ylmethyl}-amine; or
[4-(4-[1,2,3]Triazol-1-yl-butyl)-phenyl]-{2-[2-(3-trifluoromethoxy-phenyl)-vinyl]-oxazol-4-ylmethyl}-amine.

Another embodiment of the invention are the compounds of formula (I), wherein
R$^1$ is halogen;
—O-alkyl; or
alkyl, all alkyl groups being optionally once or several times substituted with halogen; and
R$^2$ is halogen;
R$^3$ is hydrogen; and
R$^4$ is hydrogen; or
methyl;
V is —CH$_2$—; and
—W—X—Y— is —(CH$_2$)$_4$—;

or their pharmaceutically acceptable salts.

Such compounds are for example:

{2-[2-(2-Fluoro-4-trifluoromethyl-phenyl)-vinyl]-oxazol-4-ylmethyl}-[4-(4-[1,2,3]triazol-1-yl-butyl)-phenyl]-amine;

{2-[2-(3,4-Dichloro-phenyl)-vinyl]-oxazol-4-ylmethyl}-[4-(4-[1,2,3]triazol-1-yl-butyl)-phenyl]-amine;

{2-[2-(4-Fluoro-2-trifluoromethyl-phenyl)-vinyl]-oxazol-4-ylmethyl}-[4-(4-[1,2,3]triazol-1-yl-butyl)-phenyl]-amine;

{2-[(E)-2-(2,4-Difluoro-phenyl)-vinyl]-oxazol-4-ylmethyl}-[4-(4-[1,2,3]triazol-1-yl-butyl)-phenyl]-amine; or {2-[(E)-2-(4-Chloro-2-fluoro-phenyl)-vinyl]-oxazol-4-ylmethyl}-[4-(4-[1,2,3]triazol-1-yl-butyl)-phenyl]-amine.

Still another embodiment of the invention are the compounds of formula (I), wherein
$R^1$ and $R^2$ together with the carbon atoms to which they are attached form a 5 or 6 membered heterocyclic ring; and
$R^3$ is hydrogen; or
halogen;
$R^4$ is hydrogen; or
methyl;
V is —$CH_2$—; and
—W—X—Y— is —$(CH_2)_4$—;

or their pharmaceutically acceptable salts.

Such compounds are for example:
[2-(2-Benzo[1,3]dioxol-5-yl-vinyl)-oxazol-4-ylmethyl]-[4-(4-[1,2,3]triazol-1-yl-butyl)-phenyl]-amine;
{2-[2-(2,2-Difluoro-benzo[1,3]dioxol-5-yl)-vinyl]-oxazol-4-ylmethyl}-[4-(4-[1,2,3]triazol-1-yl-butyl)-phenyl]-amine; or
[2-(2-Benzo[1,3]dioxol-5-yl-vinyl)-oxazol-4-ylmethyl]-methyl-[4-(4-[1,2,3]triazol-1-yl-butyl)-phenyl]-amine.

Still another embodiment of the invention are the compounds of formula (I), wherein
$R^1$ is halogen;
—O-alkyl;
—S-alkyl; or
alkyl, all alkyl groups being optionally once or several times substituted with halogen; and
$R^2$, $R^3$ are both hydrogen; and
$R^4$ is hydrogen; or
methyl;
V is —C(O)—; and
—W—X—Y— is —$(CH_2)_4$—;

or their pharmaceutically acceptable salts.

Such compounds are for example:
2-[2-(4-Trifluoromethyl-phenyl)-vinyl]-oxazole-4-carboxylic acid [4-(4-[1,2,3]triazol-1-yl-butyl)-phenyl]-amide;
2-[2-(4-Trifluoromethyl-phenyl)-vinyl]-oxazole-4-carboxylic acid methyl-[4-(4-[1,2,3]triazol-1-yl-butyl)-phenyl]-amide;
2-[2-(4-Trifluoromethoxy-phenyl)-vinyl]-oxazole-4-carboxylic acid [4-(4-[1,2,3]triazol-1-yl-butyl)-phenyl]-amide;
2-[2-(4-Trifluoromethoxy-phenyl)-vinyl]-oxazole-4-carboxylic acid methyl-[4-(4-[1,2,3]triazol-1-yl-butyl)-phenyl]-amide;
2-[(E)-2-(4-Difluoromethoxy-phenyl)-vinyl]-oxazole-4-carboxylic acid [4-(4-[1,2,3]triazol-1-yl-butyl)-phenyl]-amide; or
2-[(E)-2-(4-Difluoromethoxy-phenyl)-vinyl]-oxazole-4-carboxylic acid methyl-[4-(4-[1,2,3]triazol-1-yl-butyl)-phenyl]-amide.

Still another embodiment of the invention are the compounds of formula (I), wherein
$R^1$ is halogen;
—O-alkyl; or
alkyl, all alkyl groups being optionally once or several times substituted with halogen; and
$R^2$ is halogen;
$R^3$ is hydrogen; and
$R^4$ is hydrogen; or
methyl;
V is —C(O)—; and
—W—X—Y— is —$(CH_2)_4$—;

or their pharmaceutically acceptable salts.

Still another embodiment of the invention are the compounds of formula (I), wherein
$R^1$ and $R^2$ together with the carbon atoms to which they are attached form a 5 or 6 membered heterocyclic ring; and
$R^3$ is hydrogen; or
halogen;
$R^4$ is hydrogen; or
methyl;
V is —C(O)—; and
—W—X—Y— is —$(CH_2)_4$—;

or their pharmaceutically acceptable salts.

Such compounds are for example:
2-[(E)-2-(2,2-Difluoro-benzo[1,3]dioxol-5-yl)-vinyl]-oxazole-4-carboxylic acid methyl-[4-(4-[1,2,3]triazol-1-yl-butyl)-phenyl]-amide; or
2-[(E)-2-(2,2-Difluoro-benzo[1,3]dioxol-5-yl)-vinyl]-oxazole-4-carboxylic acid [4-(4-[1,2,3]triazol-1-yl-butyl)-phenyl]-amide.

Still another embodiment of the invention are the compounds of formula (I), wherein
$R^1$ is halogen;
—O-alkyl;
—S-alkyl; —S(O)-alkyl; —S(O)$_2$-alkyl
—N-alkyl; or
alkyl, all alkyl groups being optionally once or several times substituted with halogen; and
$R^2$ is hydrogen; or
halogen; and
$R^3$ is hydrogen;
$R^4$ is hydrogen; or
methyl; and
V is —$CH_2$—; or
—C(O)—; and
—W—X—Y— is —O—$(CH_2)_3$—; —C(O)—$(CH_2)_3$—; —S—$(CH_2)_3$—; —S(O)$_2$—$(CH_2)_3$—; —S(O)—$(CH_2)_3$—; —S(O)$_2$—NH—$(CH_2)_2$—; —NH—C(O)—$(CH_2)_2$—; —C(O)—NH—$(CH_2)_2$—; —$CH_2$—NH—$(CH_2)_2$—; —CH=CH—$(CH_2)_2$— or —$CH_2$—CH=CH—CH2-;

or their pharmaceutically acceptable salts.

Such compounds are for example:
[4-(3-[1,2,3]Triazol-1-yl-propoxy)-phenyl]-{2-[2-(4-trifluoromethyl-phenyl)-vinyl]-oxazol-4-ylmethyl}-amine;
Methyl-[4-(3-[1,2,3]triazol-1-yl-propoxy)-phenyl]-{2-[2-(4-trifluoromethyl-phenyl)-vinyl]-oxazol-4-ylmethyl}-amine;
[4-(3-[1,2,3]Triazol-1-yl-propoxy)-phenyl]-{2-[2-(4-trifluoromethoxy-phenyl)-vinyl]-oxazol-4-ylmethyl}-amine;
[4-(3-[1,2,3]Triazol-1-yl-propoxy)-phenyl]-{2-[2-(4-trifluoromethylsulfanyl-phenyl)-vinyl]-oxazol-4-ylmethyl}-amine;
{2-[2-(4-Chloro-phenyl)-vinyl]-oxazol-4-ylmethyl}-[4-(3-[1,2,3]triazol-1-yl-propoxy)-phenyl]-amine;
2-[2-(4-Trifluoromethyl-phenyl)-vinyl]-oxazole-4-carboxylic acid [4-(3-[1,2,3]triazol-1-yl-propoxy)-phenyl]-amide;
2-[2-(4-Trifluoromethoxy-phenyl)-vinyl]-oxazole-4-carboxylic acid [4-(3-[1,2,3]triazol-1-yl-propoxy)-phenyl]-amide;

2-[2-(4-Trifluoromethoxy-phenyl)-vinyl]-oxazole-4-carboxylic acid methyl-[4-(3-[1,2,3]triazol-1-yl-propoxy)-phenyl]-amide; or

[4-(4-[1,2,3]Triazol-1-yl-but-1-enyl)-phenyl]-{2-[2-(4-trifluoromethanesulfinyl-phenyl)-vinyl]-oxazol-4-ylmethyl}-amine.

Still another embodiment of the invention are the compounds of formula (I), wherein
$R^1$ and $R^2$ together with the carbon atoms to which they are attached form a 5 or 6 membered heterocyclic ring; and
$R^3$ is hydrogen; or
halogen;
$R^4$ is hydrogen; or
methyl;
V is —$CH_2$—; or
—C(O)—; and
—W—X—Y— is —O—$(CH_2)_3$—; —C(O)—$(CH_2)_3$—; —S—$(CH_2)_3$—; —$S(O)_2$—$(CH_2)_3$—; —S(O)—$(CH_2)_3$—; —$S(O)_2$—NH—$(CH_2)_2$—; —NH—C(O)—$(CH_2)_2$—; —C(O)—NH—$(CH_2)_2$—; —$CH_2$—NH—$(CH_2)_2$—; —CH=CH—$(CH_2)_2$— or —$CH_2$—CH=CH—$CH_2$—;

or their pharmaceutically acceptable salts.

Still another embodiment of the invention are the compounds of formula (I):
[4-(2-[1,2,3]Triazol-1-yl-ethoxymethyl)-phenyl]-{2-[2-(4-trifluoromethoxy-phenyl)-vinyl]-oxazol-4-ylmethyl}-amine;
[4-(2-[1,2,3]Triazol-1-yl-ethoxymethyl)-phenyl]-{2-[2-(4-trifluoromethyl-phenyl)-vinyl]-oxazol-4-ylmethyl}-amine; or
[4-(4-[1,2,3]Triazol-1-yl-butyl)-phenyl]-{2-[(E)-2-(4-trifluoromethanesulfinyl-phenyl)-vinyl]-oxazol-4-ylmethyl}-amine.

Still another embodiment of the invention is a process for the manufacture of the compounds of formula (I), wherein
1. a compound of formula (VI)

(formula VI)

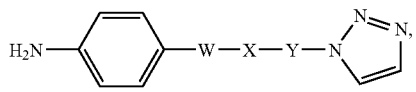

wherein W, X and Y have the meaning given herein before, is reacted with 1a) either a compound of formula (VII)

(formula VII)

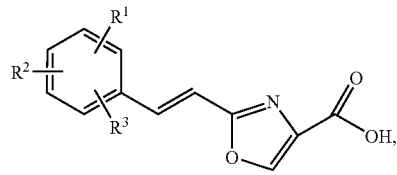

wherein $R^1$, $R^2$ and $R^3$ have the meaning given herein before, to give a compound of formula (I) wherein V is —C(O)— and $R^4$ is hydrogen; or 1b) said compound of formula (VI) is reacted with a compound of formula (V), formula (V)

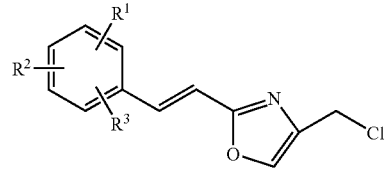

wherein $R^1$, $R^2$ and $R^3$ have the meaning given herein before, to give a compound of formula (I) wherein V is —$CH_2$— and $R^4$ is hydrogen; and 2. if desired, the compound obtained in 1a) is further reacted with a suitable alkyl halide and the compound obtained in 1b) is further reacted with a suitable aldehyde to give the corresponding compound of formula (I) wherein $R^4$ is alkyl;

3. said compound of formula (I), obtained from 1a), 1b) or 2. is isolated from its reaction mixture; and 4. if desired, converted into a pharmaceutically acceptable salt.

The aniline derivatives of the general formula (I), or a pharmaceutically acceptable salt thereof, may be prepared by any process known to be applicable for the preparation of chemically-related compounds by the one skilled in the art. Such processes, when used to prepare the aniline derivatives of formula (I), or a pharmaceutically-acceptable salt thereof, are provided as a further feature of the invention and are illustrated by the following schemes 1 and 2, in which, unless otherwise stated, $R^1$, $R^2$, $R^3$ and $R^4$ have the significance given herein before. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

The manufacture of the compounds of formula (I) varies according to the nature of "V" in formula (I). The compounds of the present invention wherein "V" is $CH_2$ can be prepared according to scheme 1, and are named (Ia). The substituent $R^{4'}$ in the aldehyde $R^{4'}$CHO, scheme 1 has the meaning of $R^4$, therefore hydrogen or alkyl. The different nomenclature however illustrates that $R^{4'}$ always lacks one carbon-atom with respect to $R^4$, since one carbon-atom in $R^4$ of compounds of formula (Ia) comes from the carbonyl group of $R^{4'}$—CHO.

scheme 1

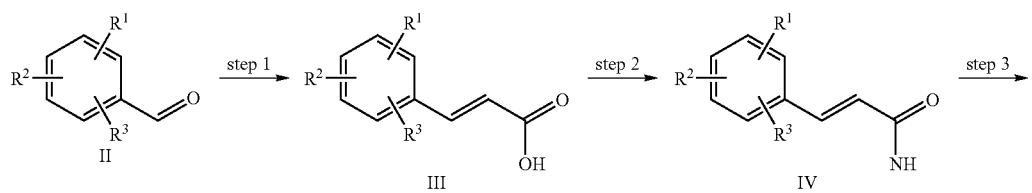

-continued

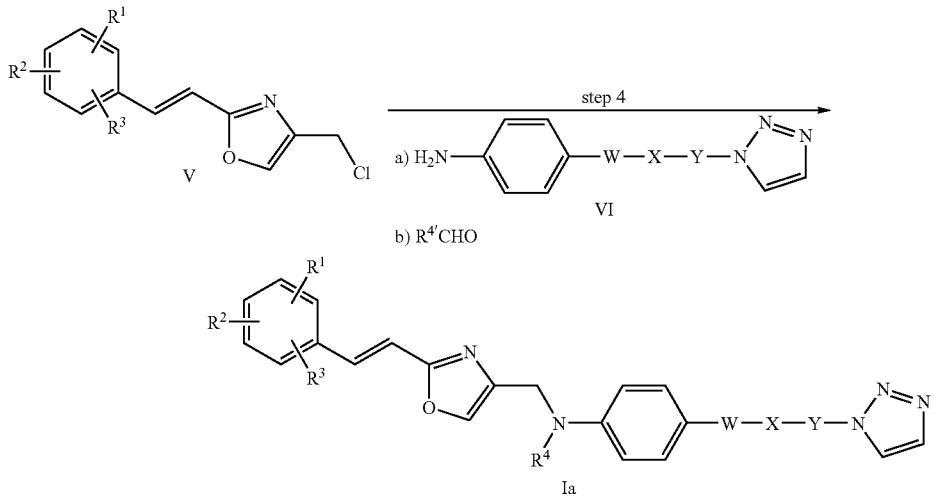

A preferred method for the synthesis of the compounds of formula (Ia) starts from the corresponding benzaldehydes of formula (II). Step 1 of the reaction sequence (scheme 1) is a Knoevenagel condensation with malonic acid and concomitant decarboxylation, yielding the acrylic acid derivatives of formula (III). The reaction is typically carried out in solvents like pyridine, N-Methylpyrrolidin, acetonitrile, N,N-dimethylformamide and mixtures thereof at temperatures up to 140° C. or under reflux. Typically used bases are piperidine, triethylamine and diisopropylamine.

In step 2, scheme 1 the obtained compounds of formula (III) are converted into their corresponding amides of formula (IV), using methods well known to someone skilled in the art, e.g. by activating the carboxylic group in said compounds of formula (III) with oxalyl chloride in solvents like tetrahydrofuran, dichloromethane, N,N-dimethylformamide and mixtures thereof at temperatures varying from −30° C. to 40° C. The addition of aqueous ammonia yields the amides of formula (IV).

With step 3, scheme 1 the chlorides of formula (V) are synthesized using commonly known methods. The amides of formula (IV) and 1,3-dichloroacetone are subjected to a condensation/dehydration sequence yielding the compounds of formula (V). Typical solvents for reactions of this kind are toluene, benzene, acetone and chloroform. If desired the reaction can be carried out under solvent free conditions. The reaction temperatures may vary from 50° C. to 150° C.

In step 4, scheme 1 the aniline derivatives of formula (Ia) can be obtained by reactions well known to someone skilled in the art, e.g. by alkylation of the anilines of formula (VI) with compounds of formula (V) according to reaction a) of step 4. Typically the alkylation is carried out in solvents like N,N-dimethyl formamide, methanol, ethanol and isopropanol. Typical bases for this reaction are sodium methylate, sodium hydride or lithium diisopropyl amide. The reaction temperatures may vary from 50° C. to 150° C. When the synthesis is stopped after reaction a) the derivatives of formula (Ia) wherein $R^4$ is hydrogen are obtained.

When reaction b) is carried out subsequent to a) the amines of formula (Ia) wherein $R^4$ is alkyl can be obtained using reactions well known to someone skilled in the art, such as e.g. but not limited to reductive amination of the secondary amines obtained from a) in step 4. The reaction represents a condensation with aldehydes which is typically achieved in solvents like acetonitrile, N,N-dimethylformamide, methanol or ethanol and at temperatures between 20° C. and 150° C. Reducing agents typically employed are e.g. sodium cyanoborohydride ($NaCNBH_3$), sodium borohydride ($NaBH_4$) or lithium aluminium hydride ($LiAlH_4$).

A preferred method for the synthesis of the derivatives of formula (I), wherein V is —C(O)— is described in scheme 2. The derivatives of formula (I), wherein V is —C(O)— are named Ib in scheme 2. The substituent $R^{4'''}$ in scheme 2 has the meaning of $R^4$ without hydrogen, therefore $R^{4'''}$ is alkyl as defined herein before.

scheme 2

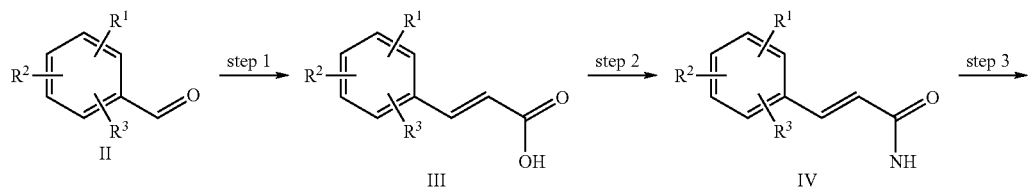

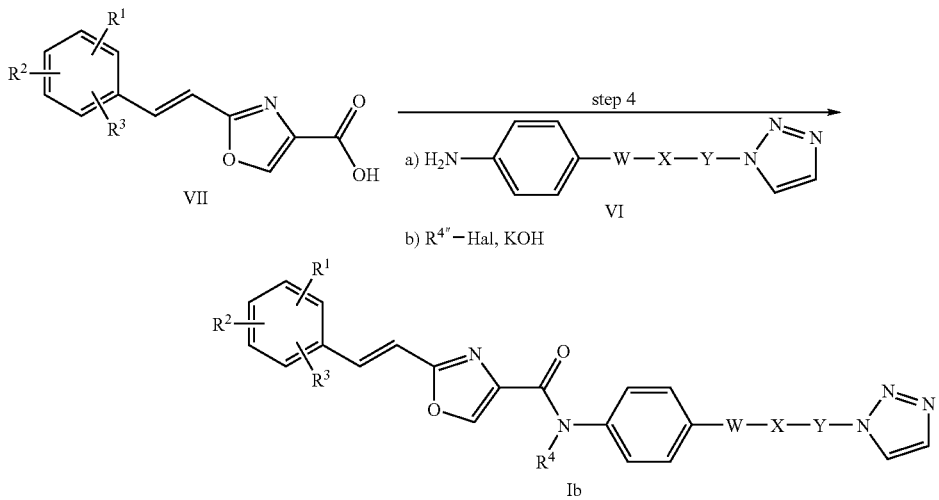

Starting materials are the corresponding benzaldehydes of formula (II), wherein $R^1$, $R^2$ and $R^3$ have the meaning given herein before. Step 1 of the reaction sequence in scheme 2 is a Knoevenagel condensation with malonic acid and concomitant decarboxylation, yielding acrylic acids of formula (III). The reaction is typically carried out in solvents like pyridine, N-Methylpyrrolidin, acetonitrile, N,N-dimethylformamide and mixtures thereof at temperatures up to 140° C. or under reflux. Typically used bases are piperidine, triethylamine and diisopropylamine.

In step 2, scheme 2 the acrylic acids of formula (III) are converted into their corresponding amides of formula (IV) using methods well known to someone skilled in the art, e.g. by activating the carboxylic group in compounds of formula (III) with oxalyl chloride in solvents like tetrahydrofuran, dichloromethane, N,N-dimethylformamide and mixtures thereof at temperatures varying from –30° C. to 40° C. The addition of aqueous ammonia yields said amides of formula (IV).

In step 3, scheme 2 the carboxylic acids of formula (VII) are obtained. This reaction is typically performed in a three step procedure, starting with the reaction of the amides of formula (IV) with 3-Bromo-2-oxo-propionic acid esters which is typically performed in solvents like THF, acetonitrile, methanol or ethanol at temperatures between 20° C. and 150° C. or at reflux. Typically used bases are sodium bicarbonate ($NaHCO_3$), potassium carbonate ($K_2CO_3$), sodium hydroxide (NaOH) and potassium hydroxide (KOH). In the second step the cyclization is achieved in the presence of e.g. trifluoroacetic acid anhydride in solvents like THF, acetonitril, methanol or ethanol at temperature varying from 0° C. to 150° C. In the third step hydrolysis of the resulting esters is achieved by standard methods for someone skilled in the art. Typically used bases are e.g. NaOH, KOH, lithium hydroxide (LiOH) in solvents like water, THF, methanol, ethanol or mixtures thereof at temperature between 0° C. and 150° C., yielding the carboxylic acids of formula (VII).

In step 4, scheme 2 the obtained carboxylic acids of formula (VII) are reacted with anilines of formula (VI) using standard methods for someone skilled in the art, e.g. by activating the carboxylic group in the compounds of formula. (VII) with EDCI, Hydroxybenzotriazole (HOBt) or oxalyl chloride in solvents like THF, dichloromethane, N,N-dimethylformamide or mixtures thereof and at temperatures varying from –30° C. to 40° C., yielding derivatives of formula (Ib) wherein V is —C(O)— and R4 is hydrogen (reaction a), step 4).

When the synthesis is further proceeded by reaction b) in step 4 the compounds of formula (Ib) wherein $R^4$ is alkyl are obtained. The alkylation of amides is typically achieved with alkyl halides such as for example the alkyl halides of the formula $R^{4''}$-Hal, wherein "Hal" is a halogen-atom, preferably iodine or bromine and $R^{4''}$ is as defined above (s. step 4, scheme 2). The reaction is carried out in the presence of a base like NaOH, KOH, triethyl amine ($NEt_3$) or sodium hydride (NaH) and in solvents like acetone, ethyl acetate, methanol, ethanol, N,N-dimethylformamide or mixtures thereof at temperatures varying from 0° C. to 150° C.

Still another embodiment of the invention are the compounds of the general formula (Ic), formula (Ic)

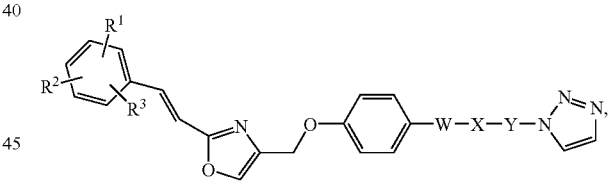

wherein
$R^1$, $R^2$ and $R^3$ have the significance given above; and
W is —$CH_2$—; or
a direct bond,
X is —NH—, —O—, —S—, —SO—, —$SO_2$—, —CO—, —CONH—, —NHCO—, —$SO_2NH$—, —CH=CH—;
Y is —$(CH_2)_n$—;
n is 1 or 2 or 3; and their pharmaceutically acceptable salts.

The derivatives of the general formula (Ic), as well as the corresponding starting materials, may be prepared by reactions analogue to those described in scheme 1. Such modifications of the reactions described in scheme 1 that are necessary to obtain the compounds of formula (Ic), e.g. using the compounds of formula (VIII) instead of the compounds of formula (VI) in step 4 of scheme 1, are within the ordinary skill of an organic chemist. Processes, when used to prepare the derivatives of formula (Ic), or a pharmaceutically-acceptable salt thereof, are provided as a further feature of the invention. One preferred method to obtain the compounds of formula (Ic) comprises reacting
(a) the compounds of formula (VIII)

formula (VIII)

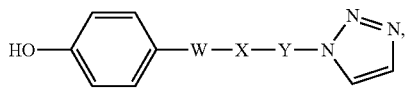

wherein
W is —$CH_2$—; or
a direct bond,
X is —NH—, —O—, —S—, —CO—, —CONH—, —NHCO—, —$SO_2$NH—, —CH=CH—;
Y is —$(CH_2)_n$—; and
n is 1 or 2 or 3;
with a compound of formula (V)

formula (V)

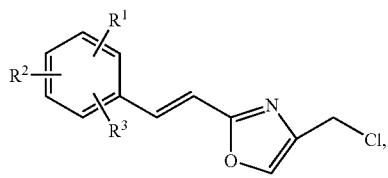

wherein $R^1$, $R^2$ and $R^3$ have the significance given herein before, to give the respective compound of formula (Ic);
(b) said compound of formula (Ic) is isolated from the reaction mixture, and
(c) if desired a group —S— in —W—X—Y— is oxidised to a group —SO— or —$SO_2$—, and
(d) if desired, the compounds obtained from a)–c) are converted into a pharmaceutically acceptable salt.

The synthesis of the compounds of formula (V) is described in steps 1 to 3 of scheme 1 and the accompanying description hereinbefore. The oxazole derivatives of formula (Ic) can then be obtained by reactions well known to someone skilled in the art, e.g. by alkylation of the compounds of formula (VIII), wherein —W—X—Y— has the meaning given herein before, with compounds of formula (V). Typically the alkylation is carried out in the presence of potassium iodide or sodium iodide in solvents like methanol, ethanol, isopropanol and N,N-dimethylformamide. Typical bases for this reaction are sodium methylate, sodium hydride or lithium diisopropyl amide. The reaction temperatures may vary from 50° C. to 150° C.

The compounds of formula (I) or (Ic) can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds of formula (I) or (Ic) and their pharmaceutically acceptable salts possess valuable pharmacological properties. It has been found that said compounds inhibit the HER-signalling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above. The activity of the present compounds as HER-signalling pathway inhibitors is demonstrated by the following biological assay:

Assay Description

HCT116 cells (human colon carcinoma cell line) were cultivated in RPMI 1640, 2.5% FCS, 2 mM Glutamine, 100 u/ml Penicillin, 100 ug/ml Streptomycin. For the assay the cells were seeded in 384 well plates, 1000 cells per well, in the same medium The next day compounds (dissolved 10 mM in DMSO) were added in various concentrations ranging from 3 uM to 0.15 nM. After 5 days the MTT assay was done mainly according to the instructions of the manufacturer (Cell proliferation kit I, MTT, from Roche Molecular Biochemicals). In brief: MTT labeling reagent was added to a final concentration of 0.5 mg/ml, added and incubated for 4 hrs at 37° C., 5% $CO_2$. During this incubation time purple formazan crystals are formed. After addition of the solubilization solution (20% SDS in 0.02 M HCl) the plates were incubated overnight at 37° C., 5% $CO_2$. After careful mixing plates were measured in Victor 2 (scanning multiwell spectrophotometer, Wallac) at 550 nm.

A decrease in number of living cells results in a decrease in the total metabolic activity in the sample. The decrease directly correlates to the amount of purple color resulting from the solubilization of the purple formazan crystals.

Materials:
HCT116 1000 cells in 60 ul per well of 384 well plate (Greiner)
Medium: RPMI 1640, 2.5% FCS, glutamine, pen/strep.
Incubate 1 day at 37° C.
Induction:
Dilution of compound in DMSO: 3 ul 10 mM+27 ul DMSO, dilute 1:3
Add 2 ul of compound dilution row to 95 ul of medium
Add 10 ul of compound dilution to 60 ul medium in test plate results in 0.3% DMSO per well
Incubate 120 h (5 days) at 37° C., 5% $CO_2$
Analysis:
Add 7 ul MTT (5 mg7 ml/well), incubate 4 h at 37° C.
Add 30 ul lysis buffer (20% SDS, 0.04N HCl) per well
Incubate overnight at 37° C.
Measurement:
Victor 2 (scanning multiwell spectrophotometer, Wallac), at 550 nm
Determination of IC50 was done using XL-fit.
Results:

| Examples | IC50 HCT116 [nM] |
|---|---|
| 1, 2, 3, 5, 8, 9, 14, 24, 25, 31, 34, 36, 29 | <20 |
| 11, 12, 37 | 20–40 |
| 4, 6, 7, 10, 13, 15, 16, 17, 18, 19, 20, 21, 22, 23, 26, 27, 28, 30, 32, 33, 35 | >40 |

In Vivo Assay on Tumor Inhibition:

To generate primary tumors, NSCLC (e.g. QG56, A549, Calu-3) cells (4–5.0×$10^6$ in a volume of 100 μl) are injected subcutaneously into the left flank of female SCID beige or BALB/c nude mice using a 1 ml syringe and a 26 G needle.

The tumor cells are originally obtained from the NCI and deposited in a working cell bank. The cells are thawed and expanded in vitro before use in the experiment. Mice are assigned to the treatment groups 14–21 days after cell injection. For grouping (n=10–15 mice per group), the animals are randomized to get a similar mean primary tumor volume of ca. 100–150 mm³ per group. The test compounds are administered orally once per day as a suspension in 7.5% gelatine 0.22% NaCl with an administration volume of 10 ml/kg based on actual body weights. Treatment is initiated one day after staging, and carried out until day 20–50, the final day of the study. The subcutaneous primary tumors are measured twice weekly, starting prior to randomisation, in two dimensions (length and width) using an electronic caliper. The volume of the primary tumor is calculated using the formula: $V[mm^3]$=(length [mm]×width [mm]×width [mm])/2. In addition, the body weight of all animals is recorded at least twice weekly. Finally, at the end of the study the tumors are explanted and weighed.

The compounds according to this invention and their pharmaceutically acceptable salts can be used as medicaments, e.g. in the form of pharmaceutical composition. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Preferred pharmaceutical compositions comprise the following:

a) Tablet Formulation (Wet Granulation):

| Item | Ingredients | Mg/tablet | | | |
|---|---|---|---|---|---|
| 1. | Compound of formula (I) or (Ic) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) or (Ic) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Microsuspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 µm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenise.

The above described preparation yields micro-suspensions of the compounds of formula I with particle sizes between 1 and 10 µm. The suspensions are suitable for oral applications and can be used in the in vivo assay described above.

Pharmaceutical compositions containing a compound of formula (I) or (Ic) or a pharmaceutically acceptable salt thereof and a therapeutically inert carrier are also an object of the present invention, as is a process for their production, which comprises bringing one or more compounds of formula (I) or (Ic) and/or pharmaceutically acceptable salts and, if desired, one or more other therapeutically valuable substances into a galenical administration form together with one or more therapeutically inert carriers.

In accordance with the invention compounds of formula (I) or (Ic) as well as their pharmaceutically acceptable salts are useful in the control or prevention of illnesses. Based on their HER-signalling pathway inhibition and their antiproliferative activity, said compounds are useful for the treatment of diseases such as cancer in humans or animals and for the production of corresponding medicaments. The dosage depends on various factors such as manner of administration, species, age and/or individual state of health.

The following examples and references are provided to aid the understanding of the present invention, the true scope of which is set forth in the appended claims. It is understood that modifications can be made in the procedures set forth without departing from the spirit of the invention.

EXAMPLES

Experimental Procedures

A: Starting Materials

Preparation of
1-[4-(4-Nitro-phenyl)-butyl]-1H-[1,2,3]triazole

A solution of p-nitrophenylbutanol (5 g, 25.61 mmol) in ethyl acetate (200 ml) is treated with methanesulfonyl chloride (3.52 g, 30.73 mmol) at 0° C. The resulting suspension is stirred for 30 min at this temperature and for 1 h at room temperature. The mixture is washed with ice water and brine, dried over $Na_2SO_4$ and evaporated to dryness. The resulting oily residue crystallizes on cooling yielding 7.62 g of a yellow solid.

To a suspension of the mesylate (6.53 g, 23.9 mmol) in 2-methyl-2-butanol (100 ml) 1H-1,2,3-triazole (2.46 g, 35.6 mmol), KI (0.392 g, 23.6 mmol) and NaOH (1.44 g, 36 mmol) are added and the mixture stirred for 3 h at room temperature. After evaporation of the solvent the mixture is taken up in toluene (150 ml) and washed with water. The toluene layer is evaporated to dryness and the residue dissolved in ethyl acetate/isopropyl ether (2/1, 15 ml) followed by the addition of methane sulfonic acid (0.3 g). After stirring for 1 h at room temperature the resulting precipitate is filtered, washed wit ethyl acetate/isobutyl ether (1:1) and dried yielding 1-[4-(4-nitro-phenyl)-butyl]-1H-[1,2,3]triazole methanesulfonate as a yellow solid which can be used without further purification. Yield 3.5 g (55.5%)

MS: M=246.2 (API+) $^1$H-NMR (400 MHz, $CDCl_3$): 1.73 (m, 2H), 2.03 (m, 2H), 2.79 (t, J=7.6 Hz, 2H) 2.90 (s, 3H), 4.60 (t, J=7.2 Hz, 2H), 7.32 (d, J=8.5 Hz, 2H), 8.14 (d, J=8.5 Hz, 2H), 8.21 (s, 1H), 8.25 (s, 1H), 9.54 (br, 1H)

Preparation of
4-(4-[1,2,3]Triazol-1-yl-butyl)-phenylamine

1-[4-(4-Nitro-phenyl)-butyl]-1H-[1,2,3]triazole (2.89 g, 11.74 mmol) is hydrogenated in a mixture of methanol/THF (1:1, 50 ml) in the presence of palladium on charcoal (10%, 0.5 g) for 5 h. After filtration solvents are removed in vacuo yielding 4-(4-[1,2,3]triazol-1-yl-butyl)-phenylamine as a yellow gum. Yield 2.03 g (80%)

MS: M=217.3 (API+) $^1$H-NMR (400 MHz, $CDCl_3$): 1.62 (m, 2H), 1.91 (m, 2H), 2.63 (t, J=7.5 Hz, 2H), 4.38 (t, J=7.0 Hz, 2H), 7.15 (d, J=8.3 Hz, 2H), 7.41 (d, J=8.3 Hz, 2H), 7.52 (s, 1H), 7.69 (s, 1H)

Preparation of
1-(3-Chloro-propoxy)-4-nitro-benzene

4-Nitrophenol (69.56 g, 0.5 mol), potassium carbonate (138.21 g, 1 mol) and 1-bromo-3-chloro propane (236.16 g, 1.5 mol) are refluxed in methyl ethyl ketone (800 ml) for 24 h. After filtration solvents are removed, the residue dissolved in ethyl acetate (1000 ml) and washed with NaOH (1M, 150 ml) and water (2×200 ml). Drying over sodium sulfate and concentration in vacuo yields 1-(3-Chloro-propoxy)-4-nitro-benzene as a yellow liquid.

Yield 79 g (73%). $^1$H-NMR (400 MHz, [$D_6$]-DMSO): 2.23 (m, 2H), 3.82 (t, J=6.5 Hz, 2H), 4.26 (t, J=6.0 Hz, 2H), 7.17 (d, J=8.3 Hz, 2H), 8.21 (d, J=8.4 Hz, 2H)

Preparation of
1-[3-(4-Nitro-phenoxy)-propyl]-1H-[1,2,3]triazole 1-(3-Chloro-propoxy)-4-nitro-benzene (7 g, 32.5 mmol) is dissolved in 2-methyl-2-butanol (35 ml) followed by the addition of 1H-1,2,3-triazole (3.43 g, 48.7 mmol), potassium iodide (0.54 g, 3.25 mmol) and sodium hydroxide (1.95 g, 48.7 mmol). The mixture is stirred for 20 h at 120° C., evaporated to dryness and suspended in toluene. Washing with water, drying over sodium sulfate and concentration in vacuo yields a crude product, which is washed with ether yielding 1-[3-(4-nitro-phenoxy)-propyl]-1H-[1,2,3]triazole as a colorless solid. Yield 6 g (75%)

MS: M=249.3 (API+) $^1$H-NMR (400 MHz, $CDCl_3$): 2.48 (m, 2H), 4.07 (t, J=5.77 Hz, 2H), 4.64 (t, J=6.7 Hz, 2H), 6.93 (d, J=9.3 Hz, 2H), 7.56 (s, 1H), 7.72 (s, 1H), 8.20 (d, J=9.2 Hz, 2H)

Preparation of
4-(3-[1,2,3]Triazol-1-yl-propoxy)-phenylamine

1-[3-(4-Nitro-phenoxy)-propyl]-1H-[1,2,3]triazole (2.87 g, 11.6 mmol) is dissolved in THF (40 ml) and hydrogenated for 2.5 h in the presence of palladium on charcoal (10%, 500 mg). After filtration and concentration in vacuo 4-(3-[1,2,3] Triazol-1-yl-propoxy)-phenylamine can be isolated as orange oil which is precipitated with diethyl ether. Yield 2.48 g (98%)

MS: M=219.2 (API+) $^1$H-NMR (400 MHz, [$D_6$]-DMSO): 2.20 (m, 2H), 3.80 (t, J=6.1 Hz, 2H), 4.52 (t, J=7.0 Hz, 2H), 4.67 (br, 2H, $NH_2$), 6.50 (d, J=9.3 Hz, 2H), 6.64 (d, J=9.2 Hz, 2H), 7.72 (s, 1H), 8.14 (s, 1H)

Preparation of 2-[2-(4-Trifluoromethyl-phenyl)-vinyl]-oxazole-4-carboxylic acid ethyl ester To a suspension of 3-(4-trifluoromethyl-phenyl)-acrylamide (5.0 g, 23.2 mmol) and $NaHCO_3$ (7.80 g, 92.9 mmol) in THF (90 ml) 3-bromo-2-oxo-propionic acid ethyl ester (5.53 g, 25.6 mmol) is added under an argon atmosphere. The mixture is heated to reflux for 15 h when another portion of 3-bromo-2-oxo-propionic acid ethyl ester (5.53 g, 25.6 mmol) is added and stirring continued for 5 h. After cooling to r.t. the mixture is filtered, concentrated in vacuo and the resulting residue suspended in THF (20 ml). At 0° C. trifluoroacetic acid anhydride (16.3 g, 77.9 mmol) is added and the mixture stirred at room temperature for 16 h. The mixture is neutralized with sat. $NaHCO_3$, the aqueous layer extracted with ethyl acetate (2×200 ml) and the combined organic phases dried over $Na_2SO_4$ and concentrated in vacuo. The crude product is purified by flash column chromatography (ethyl acetate/heptane 4:1) yielding 2-[2-(4-trifluoromethyl-phenyl)-vinyl]-oxazole-4-carboxylic acid ethyl ester as a colorless solid. Yield 5.84 g (81%)

MS: M=312.2 (API+) $^1$H-NMR (400 MHz, [$D_6$]-DMSO): 1.31 (t, J=7.1 Hz, 3H), 4.31 (q, J=7.1 Hz, 2H), 7.39 (d, J=16.5 Hz, 1H), 7.70 (d, J=16.5 Hz, 1H), 7.78 (d, J=8.3 Hz, 2H), 7.98 (d, J=8.2 Hz, 2H), 8.89 (s, 1H)

Preparation of 2-[2-(4-Trifluoromethyl-phenyl)-vinyl]-oxazole-4-carboxylic acid

2-[2-(4-Trifluoromethyl-phenyl)-vinyl]-oxazole-4-carboxylic acid ethyl ester (1.64 g, 5.2 mmol) is dissolved in THF (20 ml), treated with aq. NaOH (1N, 10.5 ml, 10.5 mmol) and stirred for 1 h at reflux temperature. After cooling water is added and the mixture acidified with aq. HCl (3N).

The mixture is extracted with ethyl acetate (3×50 ml), the extract washed with brine (50 ml), dried over sodium sulfate and concentrated in vacuo yielding 2-[2-(4-trifluoromethyl-phenyl)-vinyl]-oxazole-4-carboxylic acid as a colorless solid. Yield 1.36 g (92%)

$^1$H-NMR (400 MHz, [D$_6$]-DMSO): 7.37 (d, J=16.5 Hz, 1H), 7.68 (d, J=16.5 Hz, 1H), 7.78 (d, J=8.2 Hz, 2H), 7.98 (d, J=8.2 Hz, 2H), 8.80 (s, 1H)

Preparation of 4-Chloromethyl-2-[2-(4-trifluoromethoxy-phenyl)-vinyl]-oxazole

A mixture of 5.00 g (3.80 ml, 26.3 mmol) 4-Trifluoromethoxy-benzaldehyde, 3.10 g (30.0 mmol) malonic acid, 0.26 g (3.0 mmol) piperidine and 15.0 ml pyridine was kept at reflux temperature until carbon dioxide development ceased (3 h). After cooling to room temperature the reaction mixture was poured onto 50 g ice and 15 ml 6N HCl. The precipitate was isolated, washed with water and dried. Yield: 5.20 g (85%) 3-(4-Trifluoromethoxy-phenyl)-acrylic acid.

$^1$H-NMR(400 MHz, D$_6$-DMSO): δ=6.57(d, 1H, 2-H), 7.40(d, 2H, 3'-/5'-H), 7.62(d, 1H, 3-H), 7.84(d, 2H, 2'-/6'-H), 12.5(br, 1H, COOH).

To a suspension of 4.90 g (21.1 mmol) 3-(4-Trifluoromethoxy-phenyl)-acrylic acid in 30.0 ml tetrahydrofurane and 0.3 ml N,N-dimethyl formamide a solution of 2.70 ml (32.0 mmol) oxalyl chloride in 5.0 ml tetrahydrofurane was added dropwise at 0° C. within 10 min. Stirring was continued at 0–5° C. for 30 min. and 2 h at room temperature thereafter. The resulting solution was cooled to 0–5° C. again and then added within 15 min. to 75 ml of a 25% aqueous ammonia solution. After stirring for 30 min. the precipitated amide was collected, washed with water and dried at 40° C. in vacuo. 4.48 g (92%) 3-(4-Trifluoromethoxy-phenyl)-acrylamide.

MS: M=232.2(API+) $^1$H-NMR (400 MHz, D$_6$-DMSO): δ=6.63(d, 1H, 2-H), 7.16(br, 1H, NH), 7.42(d, 2H, 3'-/5'-H), 7.45(d, 1H, 3-H), 7.58(br, 1H, NH), 7.70(d, 2H, 2'-/6'-H).

4.28 g (18.5 mmol) 3-(4-Trifluoromethoxy-phenyl)-acrylamide, 2.80 g (22.2 mmol) dichloro acetone and 30.0 ml toluene were kept at reflux temperature for 16 h with continuous removal of water by use of a Dean-Stark trap. After removal of solvents in vacuo, the residue was purified by chromatography on silica gel (eluent: heptane/ethyl acetate 20:1). All fractions containing the product were concentrated to a volume of 10 ml and the crystallized material isolated by filtration, washed with cold heptane and dried. 1.75 g (31%) 4-Chloromethyl-2-[2-(4-trifluoromethoxy-phenyl)-vinyl]-oxazole.

MS: M=304.2(API+) $^1$H-NMR(400 MHz, D$_6$-DMSO): δ=4.71(s, 2H, CH$_2$Cl), 7.21(d, 1H, =CH), 7.40(d, 2H, Ar—H), 7.58(d, 1H, =CH), 7.87(d, 2H, Ar—H), 8.19(s, 1H, oxazole).

Preparation of 4-Chloromethyl-2-[2-(4-difluoromethoxy-phenyl)-vinyl]-oxazole

A mixture of 10.0 g (7.68 ml, 58.1 mmol) 4-Difluoromethoxy-benzaldehyde, 6.65 g (63.9 mmol) malonic acid, 0.21 g (2.50 mmol) piperidine and 50 ml pyridine was kept at reflux temperature until carbon dioxide development ceased (3 h). After cooling to room temperature the reaction mixture was poured onto 200 g ice and 100 ml 6N HCl. The precipitate was isolated, washed with water and dried. Yield: 8.8 g (71%) 3-(4-Difluoromethoxy-phenyl)-acrylic acid.

$^1$H-NMR (400 MHz, D$_6$-DMSO): δ=6.51(d, 1H, 2-H), 7.21(d, 2H, 3'-/5'-H), 7.32(t, 1H, OCHF$_2$), 7.59(d, 1H, 3-H), 7.77(d, 2H, 2'-/6'-H), 12.4(br, 1H, COOH)

To a suspension of 8.70 g (40.6 mmol) 3-(4-Difluoromethoxy-phenyl)-acrylic acid in 60.0 ml tetrahydrofurane and 0.6 ml N,N-dimethyl formamide a solution of 5.14 ml (60.9 mmol) oxalyl chloride in 10 ml tetrahydrofurane was added dropwise at 0° C. within 10 min. Stirring was continued at 0–5° C. for 30 min. and 2 h at room temperature thereafter. The resulting solution was cooled to 0–5° C. again and then added within 15 min. to 150 ml of a 25% aqueous ammonia solution. The separating oil was collected and stirred for 30 min. with water. The precipitated amide was collected, washed with water and dried at 40° C. in vacuo. 4.7 g (54%) 3-(4-Difluoromethoxy-phenyl)-acrylamide.

MS: M=214.2 (API+). $^1$H-NMR(400 MHz, D$_6$-DMSO): δ=6.57(d, 1H, 2-H), 7.10(br, 1H, NH), 7.21(d, 2H, 3'-/5'-H), 7.29(t, 1H, CHF$_2$), 7.45(d, 1H, 3-H), 7.53(br, 1H, NH), 7.63(d, 2H, 2'-/6'-H).

4.50 g (21.1 mmol) 3-(4-Difluoromethoxy-phenyl)-acrylamide, 3.20 g (25.2 mmol) dichloro acetone and 45 ml toluene were kept at reflux temperature for 22 h with continuous removal of water by use of a Dean-Stark trap. After removal of solvents in vacuo, the residue was stirred with diethyl ether, the precipitation (some remaining starting material) sucked off and the filtrate evaporated to dryness. The residue was extracted three times with heptane, the heptane fractions evaporated and the residue dried in vacuo. 1.0 g (16%) 4-Chloromethyl-2-[2-(4-difluoromethoxy-phenyl)-vinyl]-oxazole.

MS: M=286.2(API+) $^1$H-NMR(400 MHz, D$_6$-DMSO): δ=4.70(s, 2H, CH$_2$Cl, 7.14(d, 1H, =CH), 7.22(d, 2H, Ar—H), 7.31(t, 1H, OCHF$_2$), 7.54(d, 1H, =CH), 7.80(d, 2H, Ar—H), 8.17(s, 1H, oxazole).

Preparation of 2-(2-Benzo[1,3]dioxol-5-yl-vinyl)-4-chloromethyl-oxazole

To a suspension of 50.0 g (260 mmol) 3-Benzo[1,3]dioxol-5-yl-acrylic acid in 300 ml tetrahydrofurane and 3.0 ml N,N-dimethyl formamide 44.5 ml (350 mmol) oxalyl chloride was added dropwise at 0° C. within 45 min. Stirring was continued at 0–5° C. for 30 min. and 2 h at room temperature thereafter. The resulting solution was cooled to 0–5° C. again and then added within 15 min. to 750 ml of an 25% aqueous solution of ammonia. After stirring for 30 min. the precipitated amide was collected, washed with water and dried at 40° C. in vacuo. 49.5 g (99%) 3-Benzo[1,3]dioxol-5-yl-acrylamide were obtained.

MS: M=192.2 (API+). $^1$H-NMR(400 MHz, D$_6$-DMSO): δ=6.06(s, 2H, OCH$_2$O), 6.45(d, 1H, 2-H), 6.94(d, 1H, 7'-H), 7.02(br, 1H, NH), 7.05(d, 1H, 6'-H), 7.14(s, 1H, 4'-H), 7.33(d, 1H, 3-H), 7.42(br, 1H, NH).

49.0 g (256 mmol) 3-Benzo[1,3]dioxol-5-yl-acrylamide, 44.4 g (350 mmol) dichloro acetone and 300 ml toluene were kept at reflux temperature for 48 h with continuous removal of water by applying a Dean-Stark trap. After removal of solvents in vacuo, the residue was treated with 600 ml of a 1:1 mixture of water/isopropanol. After filtration the precipitate was washed first with isopropanol, then with heptane. Drying at 40° C. in vacuo gave 51.2 g (76%) 2-(2-Benzo[1,3]dioxol-5-yl-vinyl)-4-chloromethyl-oxazole.

$^1$H-NMR(400 MHz, D$_6$-DMSO): δ=4.69(s, 2H, CH$_2$Cl), 6.07(s, 2H, OCH$_2$O), 6.94(d, 1H, 7'-H), 7.02(d, 1H, 2-H), 7.17(d, 1H, 6'-H), 7.43(s, 1H, 4'-H), 7.45(d, 1H, 3-H), 8.13(s, 1H, oxazole).

Preparation of 4-Chloromethyl-2-[2-(2,2-difluoro-benzo [1,3]dioxol-5-yl)-vinyl]-oxazole A mixture of 10.0 g (53.7 mmol) 2,2-Difluoro-benzo[1,3]dioxole-5-carbaldehyde, 6.24 g (60.0 mmol) malonic acid, 0.46 g (5.40 mmol) piperidine and 40 ml pyridine was kept at reflux temperature until carbon dioxide development ceased (3 h). After cooling to room temperature the reaction mixture was poured onto 100 g ice and 30 ml 6N HCl. The precipitate was isolated, washed with water and dried. Yield: 8.60 g (70%) 3-(2,2-Difluoro-benzo[1,3]dioxol-5-yl)-acrylic acid.

To a suspension of 8.00 g (35.1 mmol) 3-(2,2-Difluoro-benzo[1,3]dioxol-5-yl)-acrylic acid in 40 ml tetrahydrofurane and 0.4 ml N,N-dimethyl formamide, 3.86 ml (45.0 mmol) oxalyl chloride was added dropwise at 0° C. within 10 min. Stirring was continued at 0–5° C. for 30 min. and 2 h at room temperature thereafter. The resulting solution was cooled to 0–5° C. again and then added within 15 min. to 34 ml of an 25% aqueous solution of ammonia. After stirring for 30 min. the precipitated amide was collected, washed with water and dried at 40° C. in vacuo. 7.20 g (90%) 3-(2,2-Difluoro-benzo[1,3]dioxol-5-yl)-acrylamide were obtained.

$^1$H-NMR(400 MHz, D$_6$-DMSO): δ=6.59(d, 1H, 2-H), 7.14(br, 1H, NH), 7.41–7.46(m, 3H, 3-H/7'-H/6'-H), 7.53(br, 1H, NH), 7.66(s, 1H, 4'-H).

6.90 g (30.4 mmol) 3-(2,2-Difluoro-benzo[1,3]dioxol-5-yl)-acrylamide, 4.76 g (37.5 mmol) dichloro acetone and 50 ml toluene were kept at reflux temperature for 48 h with continuous removal of water by applying a Dean-Stark trap. After removal of solvents in vacuo, the residue was treated with 60 ml of a 1:1 mixture of water/isopropanol. After filtration the precipitate was washed first with isopropanol, then with heptane. Drying at 40° C. in vacuo gave 4-Chloromethyl-2-[2-(2,2-difluoro-benzo[1,3]dioxol-5-yl)-vinyl]-oxazole.

MS: M=300.0 (API+). $^1$H-NMR(400 MHz, D$_6$-DMSO): δ=4.70(s, 2H, CH$_2$Cl), 7.20(d, 1H, 2-H), 7.45(d, 1H, 7'-H), 7.55(d, 1H, 3-H),), 7.56(d, 1H, 6'-H), 7.92(s, 1H, 4'-H), 8.18(s, 1H, oxazole).

Preparation of 4-Chloromethyl-2-[2-(4-trifluoromethylsulfanyl-phenyl)-vinyl]-oxazole A mixture of 5.42 g (26.3 mmol) 4-Trifluoromethylsulfanyl-benzaldehyde, 3.12 g (30.0 mmol) malonic acid, 0.26 g (3.0 mmol) piperidine and 12.0 ml pyridine was kept at reflux temperature until carbon dioxide development ceased (5 h). The reaction mixture was poured into a solution of 50 ml ice water and 15 ml 6N HCl. The precipitate was isolated, washed with water, then with n-heptane and dried at 50° C. Yield: 5.9 g (85%) 3-(4-Trifluoromethylsulfanyl-phenyl)-acrylic acid.

MS: M=247.2 (API–) $^1$H-NMR(400 MHz, D$_6$-DMSO): δ=6.65(d, 1H, 2-H), 7.63(d, 1H, 3-H), 7.74(d, 2H, 3'-/5'-H), 7.84(d, 2H, 2'-/6'-H), 12.5(br, 1H, COOH).

To a suspension of 5.24 g (21.1 mmol) 3-(4-Trifluoromethylsulfanyl-phenyl)-acrylic acid in 30.0 ml tetrahydroftiran and 0.3 ml N,N-dimethyl formamide a solution of 2.75 ml (32.0 mmol) oxalyl chloride in 5.0 ml tetrahydrofuran was added dropwise at 0° C. within 20 min. Stirring was continued at 0–5° C. for 30 min. and 3 h at room temperature thereafter. The resulting solution was concentrated in vacuum, diluted with 200 ml water and cooled to 0–5° C. for 30 min. The precipitated amide was collected, washed with water and n-heptane and dried at 40° C. in vacuo. 4.62 g (86%) 3-(4-Trifluoromethylsulfanyl-phenyl)-acrylamide.

MS: M=248.1 (API+) $^1$H-NMR(400 MHz, D$_6$-DMSO): δ=6.72(d, 1H, 2-H), 7.21(br, 1H, NH), 7.46(d, 1H, 3-H), 7.62(br, 1H, NH), 7.73(mc, 4H, Ar—H).

4.45 g (18.0 mmol) 3-(4-Trifluoromethylsulfanyl-phenyl)-acrylamide, 2.79 g (22.0 mmol) dichloro acetone and 50.0 ml toluene were kept at reflux temperature for 30 h with continuous removal of water by use of a Dean-Stark trap. The reaction mixture was cooled for 30 min. in an ice bath and the precipitated amide (1.2 g) was removed by filtration and discarded. After removal of solvents in vacuo, the residue (5.92 g) was purified by chromatography on silica gel (eluent: heptane/ethyl acetate 1:1). All fractions containing the product were concentrated to a volume of 10 ml, n-heptane added and the crystallized material isolated by filtration, washed with cold heptane and dried. 2.02 g (35%) 4-Chloromethyl-2-[2-(4-trifluoromethylsulfanyl-phenyl)-vinyl]-oxazole.

MS: M=320.1 (API+) $^1$H-NMR(400 MHz, D$_6$-DMSO): δ=4.71(s, 2H, CH$_2$Cl), 7.30(d, 1H, =CH), 7.59(d, 1H, =CH), 7.74(d, 2H, Ar—H), 7.88(d, 2H, Ar—H), 8.21(s, 1H, oxazole).

Preparation of 2-[2-(4-Trifluoromethoxy-phenyl)-vinyl]-oxazole-4-carboxylic acid ethyl ester In an analogous manner as described for the synthesis of 2-[2-(4-trifluoromethyl-phenyl)-vinyl]-oxazole-4-carboxylic acid ethyl ester but using the corresponding starting materials 2-[2-(4-trifluoromethoxy-phenyl)-vinyl]-oxazole-4-carboxylic acid ethyl ester was obtained as white solid. Yield 6%

MS: M=328.0 (API+) $^1$H-NMR(400 MHz, CDCl$_3$): δ=1.41 (t, 3H), 4.42 (q, 2H), 6.93 (d, 1H), 7.25 (d, 2H), 7.55 (d, 2H), 7.60 (d, 1H), 8.21 (s, 1H)

Preparation of 2-[2-(4-Trifluoromethoxy-phenyl)-vinyl]-oxazole-4-carboxylic acid In an analogous manner as described for the synthesis of 2-[2-(4-trifluoromethyl-phenyl)-vinyl]-oxazole-4-carboxylic acid but using the corresponding starting material 2-[2-(4-trifluoromethoxy-phenyl)-vinyl]-oxazole-4-carboxylic acid was obtained as white solid.

Yield: 98%

MS: M=298.1 (API–)

Preparation of 2-[2-(2,2-Difluoro-benzo[1,3]dioxol-5-yl)-vinyl]-oxazole-4-carboxylic acid In an analogous manner as described for the synthesis of 2-[2-(4-trifluoromethyl-phenyl)-vinyl]-oxazole-4-carboxylic acid ethyl ester but using the corresponding starting materials 2-[2-(2,2-difluoro-benzo[1,3]dioxol-5-yl)-vinyl]-oxazole-4-carboxylic acid ethyl ester was obtained as white solid. Yield: 56%

In an analogous manner as described for the synthesis of 2-[2-(4-trifluoromethyl-phenyl)-vinyl]-oxazole-4-carboxylic acid but using the corresponding starting material 2-[2-(2,2-difluoro-benzo [1,3]dioxol-5-yl)-vinyl]-oxazole-4-carboxylic acid was obtained as white solid. Yield: 98%

1H-NMR (300 MHz, DMSO): δ=7.23(d, 1H), 7.46(d, 1H), 7.58(m, 1H), 7.60(d, 1H), 7.94(d, 1H), 8.75(s, 1H).

Preparation of 2-[2-(4-Difluoromethoxy-phenyl)-vinyl]-oxazole-4-carboxylic acid In an analogous manner as described for the synthesis 2-[2-(2,2-difluoro-benzo[1,3]dioxol-5-yl)-vinyl]-oxazole-4-carboxylic acid but using the corresponding starting materials 2-[2-(4-difluoromethoxy-phenyl)-vinyl]-oxazole-4-carboxylic acid was obtained as white solid. Yield 45%.

1H-NMR (300 MHz, CDCl3): δ=6.43(d, 1H), 6.90(d, 1H), 7.16(d, 2H), 7.51–7.65(m, 3H), 8.29(s, 1H)

Preparation of 4-(2-[1,2,3]Triazol-1-yl-ethoxymethyl)-phenylamine

A suspension of 1-chloromethyl-4-nitro-benzene (10 g, 58.3 mmol) and sodium iodide in acetone (150 ml) was refluxed for 1 h. Water was added until complete dissolution and the mixture extracted with ethyl acetate (4×100 ml). The combined organic layers were extracted with brine, dried over sodium sulfate and concentrated in vacuo yielding 13.9 g (95%) 1-Iodomethyl-4-nitro-benzene as beige crystals.

1H-NMR(400 MHz, CDCl3): δ=4.48 (s, 2H), 7.53 (d, 2H), 8.16 (d, 2H)

To a solution of 2-[1,2,3]triazol-1-yl-ethanol (5.98 g, 52.84 mmol) in dry THF (150 ml) at −50° C. sodium hydride (1.27 g, 52.84 mmol) was added and the mixture stirred for 45 min. followed by the addition of 1-iodomethyl-4-nitro-benzene (13.9 g, 52.84 mmol). The mixture was refluxed for 2 h, water (100 ml) and ethyl acetate (150 ml) were added and the resulting precipitate removed by filtration. The filtrate was concentrated and the residue purified by flash column chromatography (ethyl acetate 100%) yielding 3.6 g (27%) 1-[2-(4-nitro-benzyloxy)-ethyl]-1H-[1,2,3]triazole.

1H-NMR(400 MHz, CDCl3): δ=3.94 (t, 2H), 4.60 (s, 2H), 4.65 (t, 2H), 7.39 (d, 2H), 7.68 (s, 0.1H), 7.73 (s, 1H), 8.19 (d, 2H)

1-[2-(4-Nitro-benzyloxy)-ethyl]-1H-[1,2,3]triazole (3.6 g, 14.5 mmol) and platinum dioxide (0.4 g) were suspended in methanol (30 ml) and THF (30 ml) and hydrogenated for 3 h at 42 mbar. After filtration and concentration 3 g (95%) 4-(2-[1,2,3]triazol-1-yl-ethoxymethyl)-phenylamine were obtained as beige solid.

1H-NMR(500 MHz, CDCl3): δ=3.78 (t, 2H), 4.39 (s, 2H), 4.58 (t, 2H), 6.66 (d, 2H), 7.05 (d, 2H), 7.70 (s, 1H), 7.72 (s, 1H)

Preparation of [4-(4-[1,2,3]Triazol-1-yl-butyl)-phenyl]-carbamic acid tert-butyl ester To a solution of 4-(4-[1,2,3]triazol-1-yl-butyl)-phenylamine (15 g, 69.35 mmol) in THF (75 ml) at 0° C. lithium hexamethyldisilazide (138.75 ml, 1M in THF) was added dropwise and the mixture warmed to room temperature. A solution of di-t-butyl-dicarbonate (13.62 g, 62.4 mmol) in THF (75 ml) was then added dropwise and stirring continued for 30 min. For workup saturated ammonium chloride solution was added, the mixture extracted with ethyl acetate, dried over sodium sulfate and concentrated. The crude product was crystallized with ether and purified by column chromatography (ethyl acetate 100%) yielding 17.1 g (78%) [4-(4-[1,2,3]triazol-1-yl-butyl)-phenyl]-carbamic acid tert-butyl ester as light yellow solid.

MS: M=317.1 (API+) 1H-NMR(500 MHz, CDCl3): δ=1.51 (s, 9H), 1.62 (m, 2H), 1.91 (m, 2H), 2.59 (t, 2H), 4.37 (t, 2H), 6.57 (br, 1H), 7.05 (d, 2H), 7.27 (d, 2H), 7.49 (s, 1H), 7.68 (s, 1H)

Preparation of 4-Chloromethyl-2-[2-(3,4-dichloro-phenyl)-vinyl]-oxazole

To a suspension of 5.3 g (23.71 mmol) 3-(3,4-dichloro-phenyl)-acrylic acid in 30 ml THF and 0.3 ml N,N-dimethyl formamide a solution of 3 ml (34.55 mmol) oxalyl chloride was added dropwise at 0° C. within 45 min. Stirring was continued at 0–5° C. for 30 min. and 2 h at room temperature thereafter. The resulting solution was cooled to 0–5° C. again and then added within 15 min to 20 ml of a 25% aqueous ammonia solution. After stirring for 30 min the organic layer was separated, the aqueous layer extracted with ethyl acetate twice and the combined organic layers dried over sodium sulfate. After concentration in vacuo and washing with diethyl ether 3-(3,4-dichloro-phenyl)-acrylamide was isolated as white solid.

Yield 3.64 g(71%) 1H-NMR(400 MHz, CDCl3): δ=5.66 (br, 2H), 6.44 (d, 1H), 7.32 (d, 1H), 7.55 (d, 1H), 7.60 (s, 1H)

2.3 g (10.6 mmol) 3-(3,4-Dichloro-phenyl)-acrylamide, 4.73 g (37,2 mmol) 1,3-dichloro acetone and 15.0 ml toluene were kept at reflux temperature for 16 h with continuous removal of water by use of a Dean-Stark trap. After removal of solvents in vacuo, the residue was purified by flash column chromatography (heptane/ethyl acetate 2:1). Yield: 2.88 g (94%) 4-Chloromethyl-2-[2-(3,4-dichloro-phenyl)-vinyl]-oxazole as tan solid.

MS: M=288.1(ESI+) 1H-NMR(400 MHz, CDCl3): δ=4.54 (s, 2H), 6.89(d, 1H), 7.33–7.45(m, 3H), 7.59 (s, 1H), 7.62 (s, 1H)

Preparation of 4-Chloromethyl-2-[2-(3-trifluoromethyl-phenyl)-vinyl]-oxazole To a suspension of 5.0 g (22.67 mmol) 3-(3-trifluoromethyl-phenyl)-acrylic acid in 30 ml THF and 0.3 ml N,N-dimethyl formamide a solution of 2.5 ml (29.47 mmol) oxalyl chloride was added dropwise at 0° C. within 45 min. Stirring was continued at 0–5° C. for 30 min. and 2 h at room temperature thereafter. The resulting solution was cooled to 0–5° C. again and then added within 15 min to 20 ml of a 25% aqueous ammonia solution. After stirring for 30 min the organic layer was separated, the aqueous layer extracted with ethyl acetate twice and the combined organic layers dried over Na2SO4. After concentration in vacuo 3-(3-trifluoromethyl-phenyl)-acrylamide was isolated as white solid. Yield 4.83 g(99%)

1H-NMR(400 MHz, D6-DMSO): δ=6.76(d, 1H), 7.20(br, 1H), 7.49–7.56 (m, 2H), 7.63–7.74 (m, 2H), 7.87–7.91 (m, 2H)

2.0 g (9.3 mmol) 3-(3-Trifluoromethyl-phenyl)-acrylamide, 4.13 g (32.5 mmol) 1,3-dichloro acetone and 20.0 ml toluene were kept at reflux temperature for 16 h with continuous removal of water by use of a Dean-Stark trap. After removal of solvents in vacuo, the residue was purified by flash column chromatography (heptanes/ethyl acetate 2:1). Yield: 1.92 g (72%) 4-Chloromethyl-2-[2-(3-trifluoromethyl-phenyl)-vinyl]-oxazole as tan solid.

MS: M=288.1(ESI+) 1H-NMR(400 MHz, CDCl3): δ=4.54(s, 2H), 6.98(d, 1H), 7.50–7.71(m, 6H)

Preparation of 4-Chloromethyl-2-[2-(4-fluoro-2-trifluoromethyl-phenyl)-vinyl]-oxazole A mixture of 4-Fluoro-2-trifluoromethyl-benzaldehyde (2 g, 10.2 mmol), malonic acid (1.2 g, 11.2 mmol), piperidine (0.087 g, 1 mmol) and pyridine (7 ml) was kept at reflux temperature until carbon dioxide formation ceased (3 h).

After cooling to room temperature the reaction mixture was poured onto 40 g ice and 20 ml 6N HCl. The precipitate was isolated, washed with water and dried yielding 1.16 g (49%) 3-(4-fluoro-2-trifluoromethyl-phenyl)-acrylic acid.

MS: 233.0 (ESI−) 1H-NMR(400 MHz, [D6]DMSO): 6.63 (d,1H), 7.59–7.64 (m,1H), 7.70–7.78 (m, 2H), 8.11–8.14 (m,1H), 12.72 (br,1H)

To a suspension of 3-(4-fluoro-2-trifluoromethyl-phenyl)-acrylic acid (1.22 g, 5.2 mmol) in THF (10 ml) and N,N-dimethyl formamide (0.2 ml) a solution oxalyl chloride (0.99 g, 7.80 mmol) was added dropwise at 0° C. within 45 min. Stirring was continued at 0–5° C. for 30 min. and 3 h at room temperature thereafter. The resulting solution was cooled to 0–5° C. again and then added within 15 min. to 12 ml of a 25% aqueous ammonia solution. After stirring for 30 min. the precipitated amide was collected, washed with water and dried at 40° C. in vacuo yielding 0.53 g (40%) 3-(4-fluoro-2-trifluoromethyl-phenyl)-acrylamide.

MS: M=232.2(API+) 1H-NMR(400 MHz, CDCl3): δ=5.58 (br, 2H), 6.36 (d, 1H), 7.26 (m, 1H), 7.42 (m, 1H), 7.67 (m, 1H), 7.90 (d, 1H)

3-(4-Fluoro-2-trifluoromethyl-phenyl)-acrylamide (1.0 g, 4.29 mmol), dichloro acetone (2.18 g, 17.15 mmol) and toluene (10 ml) were kept at reflux temperature for 16 h with continuous removal of water by use of a Dean-Stark trap. After removal of solvents in vacuo, the residue was purified by chromatography on silica gel (eluent: heptane/ethyl acetate 2:1) yielding 0.93 g (71%) 4-chloromethyl-2-[2-(4-fluoro-2-trifluoromethyl-phenyl)-vinyl]-oxazole as tan solid.

MS: M=306.1 (API+) 1H-NMR(400 MHz, CDCl3): δ=4.54 (d, 2H), 6.86 (d, 1H), 7.27–7.31 (m, 1H), 7.43 (m, 1H), 7.66–7.81 (m, 3H)

Preparation of 4-Chloromethyl-2-[2-(3-trifluoromethoxy-phenyl)-vinyl]-oxazole

A mixture of 3-trifluoromethoxy-benzaldehyde (3 g, 15.78 mmol), malonic acid (2.13 g, 20.51 mmol), piperidine (0.134 g, 1.58 mmol) and pyridine (10 ml) was kept at reflux temperature until carbon dioxide formation ceased (3 h). After cooling to room temperature the reaction mixture was poured onto 60 g ice and 30 ml 6N HCl. The precipitate was isolated, washed with water and dried yielding 2.21 g (60%) 3-(3-trifluoromethoxy-phenyl)-acrylic acid.

MS: 231.2 (ESI−) ¹H-NMR(400 MHz, [D6]DMSO): 6.66 (d, 1H), 7,40 (d, 1H), 7.55 (t, 1H), 7,62 (d, 1H), 7,75 (d, 2H), 12.52 (s, 1H)

To a suspension of 3-(3-trifluoromethoxy-phenyl)-acrylic acid (2.21 g, 9.53 mmol) in THF (15 ml) and N,N-dimethyl formamide (0.2 ml) a solution oxalyl chloride (2.42 g, 19.06 mmol) was added dropwise at 0° C. within 45 min. Stirring was continued at 0–5° C. for 30 min. and 3 h at room temperature thereafter. The resulting solution was cooled to 0–5° C. again and then added within 15 min. to 12 ml of a 25% aqueous ammonia solution. After stirring for 30 min. the precipitated amide was collected, washed with water and dried at 40° C. in vacuo yielding 0.99 g (45%) 3-(3-trifluoromethoxy-phenyl)-acrylamide.

1H-NMR(400 MHz, [D6]DMSO): δ=5.66 (br, 2H), 5.47 (d, 1H), 7.22 (d, 1H), 7.36 (s, 1H), 7.36–7.43 (m, 2H), 7.62 (d,1H)

3-(3-Trifluoromethoxy-phenyl)-acrylamide (0.99 g, 4.27 mmol), dichloro acetone (1.90 g, 14.95 mmol) and toluene (8 ml) were kept at reflux temperature for 16 h with continuous removal of water by use of a Dean-Stark trap. After removal of solvents in vacuo, the residue was purified by chromatography on silica gel (eluent: heptane/ethyl acetate 2:1) yielding 0.76 g (71%) 4-chloromethyl-2-[2-(3-trifluoromethoxy-phenyl)-vinyl]-oxazole as tan solid.

1H-NMR(400 MHz, CDCl3): δ=4.54 (s, 2H), 6.93 (d, 1H), 7.19 (d, 1H), 7.35 (s, 1H), 7.39–7.53 (m, 3H), 7.64 (s, 1H)

Preparation of 4-Chloromethyl-2-[2-(4-trifluoromethanesulfinyl-phenyl)-vinyl]-oxazole A mixture of 4-chloromethyl-2-[2-(4-trifluoromethanesulfanyl-phenyl)-vinyl]-oxazole (17.6 g, 55 mmol) and 3-chloro-benzenecarboperoxoic acid (14.93 g, 60 mmol) in 200 ml dichloromethane was stirred at room temperature over night. After filtration, the filtrate was washed three times with sodium hydroxide solution, then with water, dried over sodium sulfate, filtered and evaporated. Purification on silica, after elution with heptane/ethyl acetate 5:1, yielded 5.78 g (31%) 4-chloromethyl-2-[2-(4-trifluoromethanesulfinyl-phenyl)-vinyl]-oxazole as off-white solid melting at 102–104° C.

1H-NMR(400 MHz, D6-DMSO): δ=4.72(s, 2H), 7.38(d, 1H), 7.65 (d, 1H), 7.92(d, 2H), 8.07(d, 2H), 8.23(s, 1H,).

Preparation of 1-But-3-ynyl-1H-[1,2,3]triazole

But-3-yn-1-ol (49.57 g, 707.2 mmol) and triethylamine (107.7 mL, 777 mmol, dried over KOH) were dissolved in dry dichloromethane (500 mL) under a nitrogen atmosphere and cooled to 0° C. Methanesulfonyl chloride (54.8 mL, 708 mmol), dissolved in 500 mL of dry dichloromethane was added within 90 minutes while keeping the temperature below 5° C. The mixture was stirred for 3.5 hours at room temperature, then poured onto 2.5 L of ice water. The organic phase was separated and washed with 2×500 mL of water and 1×250 mL of brine and dried over sodium sulfate. The volatiles were removed to yield 94.18 g of the methane sulfonate (631.2 mmol, 89.2%) as a yellow liquid.

A suspension of NaOH (37.86 g, 946.5 mmol), sodium iodide (94.65 g, 631.5 mmol) and 1H-[1,2,3]triazole (61.03 g, 883.6 mmol) in 2-methyl-2-butanol (750 mL) was refluxed for 1 h under an inert atmosphere. After cooling to room temperature the methane sulfonate (94.18 g, 631.2 mmol) was added within 5 minutes. The resulting suspension was then heated to reflux for 3 h, cooled to room temperature and concentrated in vacuo at 45° C. Water (500 mL) and dichloro methane (1 L) were added and the organic phase was separated, dried over sodium sulfate and the volatiles removed at 30° C. The residue was distilled at 1 mmHg. A forerun was collected at 20–70° C. The main fraction distilled at 123–129° C. as a colorless, turbid liquid. After filtration over Celite 1-but-3-ynyl-1H-[1,2,3]triazole was obtained as a colorless liquid (29.77 g, 38.9%).

¹H-NMR (CDCl₃) δ: 2.05 (t, 1H), 2.75 (dt, 2H), 4.5 (t, 2H), 7.65 (s, 1H), 7.7 (s, 1H)

Preparation of (4-Iodo-phenyl)-carbamic acid tert-butyl ester

4-Iodoaniline (3.28 g, 15 mmol) was dissolved in anhydrous THF (70 ml), cooled to 0° C. and treated with lithium hexamethyldisilazide (1M in THF, 30 ml, 30 mmol). After warming to room temperature di-tert-butyl dicarbonate (3.27 g, 15 mmol) in anhydrous THF (30 ml) was added dropwise and the mixture stirred for 2 h. The reaction was quenched by the addition of sat. NH₄Cl solution, the organic phase was separated and washed with water. After concentration the crude product was purified by flash column chromatography (ethyl acetate/heptane 4:1) yielding (4-iodo-phenyl)-carbamic acid tert-butyl ester as a tan solid (3.37 g, 70%; ~10% contamination with di-tert-butyl ester)

MS: M=318.0 (ESI−) $^1$H-NMR (400 MHz, [D$_6$]-DMSO): 1.47 (s, 9H), 7.29 (d, 2H), 7.57 (d, 2H), 9.46 (s, br, NH)

Preparation of [4-(4-[1,2,3]Triazol-1-yl-but-1-enyl)-phenyl]-carbamic acid tert-butyl ester A solution of 1-but-3-ynyl-1H-[1,2,3]triazole (0.76 g, 6.3 mmol) in anhydrous THF (50 ml) was treated with 9-BBN (0.5 M in THF, 27.6 ml, 13.8 mmol) at 0° C. and stirred for 2 h. This mixture was added to a solution of (4-iodo-phenyl)-carbamic acid tert-butyl ester (2 g, 6.3 mmol), [Pd(PPh$_3$)$_2$]Cl$_2$ (0.51 g, 0.63 mmol) and aqueous potassium carbonate (3M, 6.3 ml, 18.8 mmol) in N,N-dimethyl formamide (50 ml) and stirred for 2 h at 70° C. After cooling to room temperature ethyl acetate (100 ml) was added and the solution extracted with water (2×50 ml). The organic layer was concentrated and the crude product purified by flash column chromatography (ethyl acetate/heptane 3:1) and washing with diethyl ether to yield [4-(4-[1,2,3]triazol-1-yl-but-1-enyl)-phenyl]-carbamic acid tert-butyl ester as beige solid (0.65 g, 33%).

MS: M=315.0 (API+) $^1$H-NMR (400 MHz, CDCl$_3$): 1.46 (s, 9H), 2.71 (q, 2H), 4.50 (t, 2H), 6.09 (m, 1H), 6.31 (d, 1H), 7.22 (d, 2H), 7.38 (d, 2H), 7.69 (s, 1H), 8.12 (s, 1H), 9.34 (s, NH)

B. Products

Example 1

Preparation of [4-(4-[1,2,3]Triazol-1-yl-butyl)-phenyl]-{2-[2-(4-trifluoromethoxy-phenyl)-vinyl]-oxazol-4-ylmethyl}-amine 4-(4-[1,2,3]Triazol-1-yl-butyl)-phenylamine (0.304 g, 1 mmol) is dissolved in anhydrous N,N-dimethylformamide (5 ml) followed by the addition of sodium hydride (0.024 g, 1 mmol). After stirring for 15 min at room temperature 4-chloromethyl-2-[2-(4-trifluoromethoxy-phenyl)-vinyl]-oxazole (0.324 g, 1.5 mmol) is added and the mixture stirred for 16 h at 80° C. Ethyl acetate (25 ml) is added, the mixture is washed with brine, dried over sodium sulfate and concentrated in vacuo. After flash column chromatography (ethyl acetate/hexanes 1:1->2:1) [4-(4-[1,2,3]triazol-1-yl-butyl)-phenyl]-{2-[2-(4-trifluoromethoxy-phenyl)-vinyl]-oxazol-4-ylmethyl}-amine 1 can be isolated as a yellow solid. Yield 0.14 g (29%); m.p. 103–105° C.

MS: M=484.3 (API+) $^1$H-NMR (400 MHz, CDCl$_3$): 1.59 (m, 2H), 1.92 (m, 2H), 2.55 (t, J=7.5 Hz, 2H), 4.09 (br, 1H), 4.27 (s, 2H), 4.37 (t, J=7.2 Hz, 2H), 6.61 (d, J=8.4 Hz, 2H), 6.88 (d, J=16.4 Hz, 1H), 6.97 (d, J=8.4 Hz, 2H), 7.23 (d, J=8.2, 2H), 7.50 (m, 5H), 7.68 (s, 1H)

Example 2

[4-(4-[1,2,3]Triazol-1-yl-butyl)-phenyl]-{2-[2-(4-trifluoromethyl-phenyl)-vinyl]-oxazol-4-ylmethyl}-amine In an analogous manner as example 1 [4-(4-[1,2,3]triazol-1-yl-butyl)-phenyl]-{2-[2-(4-trifluoromethyl-phenyl)-vinyl]-oxazol-4-ylmethyl}-amine 2 can be prepared from 4-chloromethyl-2-[2-(4-trifluoromethyl-phenyl)-vinyl]-oxazole. Yield 32%; m.p. 113–115° C.

MS: M=468.3 (API+) $^1$H-NMR (400 MHz, CDCl$_3$): 1.52 (m, 2H), 1.84 (m, 2H), 2.47 (t, J=7.5 Hz, 2H), 4.03 (br, 1H), 4.21 (s, 2H), 4.30 (t, J=7.2 Hz, 2H), 6.54 (d, J=8.4 Hz, 2H), 6.91 (m, 3H), 7.41–7.58 m, 7H), 7.61 (s, 1H)

Example 3

Methyl-[4-(4-[1,2,3]triazol-1-yl-butyl)-phenyl]-{2-[2-(4-trifluoromethyl-phenyl)-vinyl]-oxazol-4-ylmethyl}-amine To a solution of [4-(4-[1,2,3]triazol-1-yl-butyl)-phenyl]-{2-[2-(4-trifluoromethyl-phenyl)-vinyl]-oxazol-4-ylmethyl}-amine 2 (0.03 g, 0.06 mmol) in acetonitrile (2 ml) formaldehyde (36%, 0.1 ml) and sodium cyanoborohydride (0.012 g, 0.019 mmol) are added. After stirring at room temperature for 10 min the pH is set to 2 by adding conc. hydrochloric acid and stirring is continued for 2 h. The solvents are evaporated, the crude product suspended in water (10 ml) and the pH adjusted to 9 with aqueous ammonia. The mixture is extracted with ethyl acetate (3×25 ml), the organic phase washed with brine and dried over sodium sulfate. After concentration in vacuo the oily residue is precipitated with heptanes to yield methyl-[4-(4-[1,2,3]triazol-1-yl-butyl)-phenyl]-{2-[2-(4-trifluoromethyl-phenyl)-vinyl]-oxazol-4-ylmethyl}-amine 3 as a light yellow solid. Yield 31 mg (100%); m.p. 112–114° C.

MS: M=482.3 (API+) $^1$H-NMR (400 MHz, CDCl$_3$): 1.60 (m, 2H), 1.93 (m, 2H), 2.56 (t, J=7.4 Hz, 2H), 3.02 (s, 3H), 4.38 (t, J=7.2 Hz, 2H), 4.43 (s, 2H), 6.72 (d, J=8.5 Hz, 2H), 7.00 (m, 3H), 7.38 (s, 1H), 7.47–7.65 (m, 8H), 7.68 (s, 1H)

Example 4

{2-[2-(4-Difluoromethoxy-phenyl)-vinyl]-oxazol-4-ylmethyl}-[4-(4-[1,2,3]triazol-1-yl-butyl)-phenyl]-amine In an analogous manner as example 1 {2-[2-(4-difluoromethoxy-phenyl)-vinyl]-oxazol-4-ylmethyl}-[4-(4-[1,2,3]triazol-1-yl-butyl)-phenyl]-amine 4 can be prepared from 4-chloromethyl-2-[2-(4-difluoromethoxy-phenyl)-vinyl]-oxazole; m.p. 101–102° C.

MS: M=466.1 (ESI+) $^1$H-NMR (400 MHz, CDCl$_3$): 1.60 (m, 2H), 1.92 (m, 2H), 2.55 (t, J=7.1 Hz, 2H) 4.27 (s, 2H), 4.37 (t, J=7.1 Hz, 2H), 6.54 (t, J=73.6 Hz, 1H), 6.61 (d, J=8.3 Hz, 2H), 6.85 (d, J=16.3 Hz, 1H), 6.97 (d, J=8.3 Hz, 2H), 7.13 (d, J=8.5 Hz, 2H), 7.45–7.53 (m, 5H), 7.68 (s, 1H)

Example 5

{2-[2-(4-Chloro-phenyl)-vinyl]-oxazol-4-ylmethyl}-[4-(4-[1,2,3]triazol-1-yl-butyl)-phenyl]-amine In an analogous manner as example 1 {2-[2-(4-chloro-phenyl)-vinyl]-oxazol-4-ylmethyl}-[4-(4-[1,2,3]triazol-1-yl-butyl)-phenyl]-amine 5 can be prepared from 4-chloromethyl-2-[2-(4-chloro-phenyl)-vinyl]-oxazole; m.p. 120–122° C.

MS: M=434.0 (ESI+) $^1$H-NMR (400 MHz, CDCl$_3$): 1.61 (m, 2H), 1.92 (m, 2H), 2.55 (t, J=7.4 Hz, 2H), 4.11 (br, 1H), 4.27 (s, 2H), 4.37 (t, J=7.1 Hz, 2H), 6.61 (d, J=8.0 Hz, 2H), 6.87 (d, J=16.4 Hz, 1H), 6.97 (d, J=8.0 Hz, 2H), 7.34–7.51 (m, 7H), 7.68 (s, 1H)

Example 6

[2-(2-Benzo[1,3]dioxol-5-yl-vinyl)-oxazol-4-ylmethyl]-[4-(4-[1,2,3]triazol-1-yl-butyl)-phenyl]-amine In an analogous manner as example 1 [2-(2-benzo[1,3]dioxol-5-yl-vinyl)-oxazol-4-ylmethyl]-[4-(4-[1,2,3]triazol-1-yl-butyl)-phenyl]-amine 6 can be prepared from 2-(2-benzo[1,3]dioxol-5-yl-vinyl)-4-chloromethyl-oxazole; m.p. 130–131° C.

MS: M=444.3 (API+) $^1$H-NMR (400 MHz, CDCl$_3$): 1.60 (m, 2H), 1.92 (m, 2H), 2.54 (t, J=7.5 Hz, 2H), 4.08 (br, 1H), 4.25 (s, 2H), 4.37 (t, J=7.2 Hz, 2H), 6.00 (s, 2H), 6.61 (d, J=8.4 Hz, 2H), 6.73 (d, J=16.3 Hz, 1H), 6.81 (d, J=8.0 Hz, 1H), 6.95–7.04 (m, 4H), 7.39–7.48 (m, 3H), 7.68 (s, 1H)

Example 7

{2-[2-(2,2-Difluoro-benzo[1,3]dioxol-5-yl)-vinyl]-oxazol-4-ylmethyl}-[4-(4-[1,2,3]triazol-1-yl-butyl)-phenyl]-amine In an analogous manner as example 1 {2-[2-(2,2-difluoro-benzo[1,3]dioxol-5-yl)-vinyl]-oxazol-4-ylmethyl}-[4-(4-[1,2,3]triazol-1-1-butyl)-phenyl]-amine 7 can be prepared from 4-chloromethyl-2-[2-(2,2-difluoro-benzo [1,3]dioxol-5-yl)-vinyl]-oxazole; m.p. 102–104° C.

MS: M=479.8 (ESI+) $^1$H-NMR (400 MHz, CDCl$_3$): 1.60 (m, 2H), 1.93 (m, 2H), 2.55 (t, J=7.5 Hz, 2H), 4.09 (br, 1H), 4.27 (s, 2H), 4.38 (t, J=7.2 Hz, 2H), 6.61 (d, J=8.3 Hz, 2H), 6.81 (d, J=16.3 Hz, 1H), 6.97 (d, J=8.4 Hz, 2H), 7.06 (d, J=8.3 Hz, 1H), 7.20–7.26 (m, 2H), 7.42–7.51 (dd, 3H), 7.68 (s, 1H)

Example 8

[4-(4-[1,2,3]Triazol-1-yl-butyl)-phenyl]-{2-[2-(4-trifluoromethylsulfanyl-phenyl)-vinyl]-oxazol-4-ylmethyl}-amine In an analogous manner as example 1 [4-(4-[1,2,3]triazol-1-yl-butyl)-phenyl]-{2-[2-(4-trifluoromethylsulfanyl-phenyl)-vinyl]-oxazol-4-ylmethyl}-amine 8 can be prepared from 4-chloromethyl-2-[2-(4-trifluoromethylsulfanyl-phenyl)-vinyl]-oxazole; m.p. 76–78° C.

MS: M=500.2 (API+) $^1$H-NMR (400 MHz, CDCl$_3$): 1.61 (m, 2H), 1.93 (m, 2H), 2.55 (t, J=7.5 Hz, 2H), 4.17 (br, 1H), 4.28 (s, 2H), 4.38 (t, J=7.2 Hz, 2H), 6.61 (d, J=8.4 Hz, 2H), 6.94–6.98 (m, 3H), 7.47–7.68 (m, 8H)

Example 9

[4-(3-[1,2,3]Triazol-1-yl-propoxy)-phenyl]-{2-[2-(4-trifluoromethyl-phenyl)-vinyl]-oxazol-4-ylmethyl}-amine In an analogous manner as example 1 [4-(3-[1,2,3]triazol-1-yl-propoxy)-phenyl]-{2-[2-(4-trifluoromethyl-phenyl)-vinyl]-oxazol-4-ylmethyl}-amine 9 can be prepared from 4-chloromethyl-2-[2-(4-trifluoromethyl-phenyl)-vinyl]-oxazole; m.p. 134–136° C.

MS: M=470.2 (API+) $^1$H-NMR (400 MHz, CDCl$_3$): 2.36 (m, 2H), 3.87 (t, J=5.7 Hz, 2H), 3.97 (br, 1H), 4.26 (s, 2H), 4.61 (t, J=6.9 Hz, 2H), 6.65 (d, J=6.8 Hz, 2H), 6.77 (d, J=6.8 Hz, 2H), 6.98 (d, J=16.4 Hz, 1H), 7.50–7.69 (m, 8H)

Example 10

Methyl-[4-(3-[1,2,3]triazol-1-yl-propoxy)-phenyl]-{2-[2-(4-trifluoromethyl-phenyl)-vinyl]-oxazol-4-ylmethyl}-amine In an analogous manner as example 3 methyl-[4-(3-[1,2,3]triazol-1-yl-propoxy)-phenyl]-{2-[2-(4-trifluoromethyl-phenyl)-vinyl]-oxazol-4-ylmethyl}-amine 10 can be prepared from [4-(3-[1,2,3]triazol-1-yl-propoxy)-phenyl]-{2-[2-(4-trifluoromethyl-phenyl)-vinyl]-oxazol-4-ylmethyl}-amine 9; m.p. 137–138° C.

MS: M=484.3 (API+) $^1$H-NMR (400 MHz, CDCl$_3$): 2.39 (m, 2H), 3.00 (s, 3H), 3.91 (t, J=5.7 Hz, 2H), 4.40 (s, 2H), 4.64 (t, J=6.8 Hz, 2H), 6.78–6.84 (m, 4H), 7.01 (d, J=16.4 Hz, 1H), 7.28 (s, 1H), 7.49–7.71 (m, 7H)

Example 11

2-[2-(4-Trifluoromethyl-phenyl)-vinyl]-oxazole-4-carboxylic acid [4-(4-[1,2,3]triazol-1-yl-butyl)-phenyl]-amide 2-[2-(4-Trifluoromethyl-phenyl)-vinyl]-oxazole-4-carboxylic acid (100 mg, 0.35 mmol), N-ethyl-N'-(3-dimethylaminopropyl)carbodiimide hydrochloride (101 mg, 0.53 mmol), 1-Hydroxybenzotriazole hydrate (73 mg, 0.53 mmol) and triethylamine (71 mg, 0.71 mmol) are suspended in dichloromethane (5 ml). After stirring at room temperature for 15 min 4-(4-[1,2,3]Triazol-1-yl-butyl)-phenylamine (84 mg, 0.39 mmol) is added and stirring is continued for 20 h. Ethyl acetate (10 ml) is added and the mixture washed with aq. HCl (1N, 10 ml), sat. NaHCO$_3$, (10 ml), dried over sodium sulfate and concentrated in vacuo. The crude product is purified by flash column chromatography (ethyl acetate/heptane 9:1) yielding 2-[2-(4-trifluoromethyl-phenyl)-vinyl]-oxazole-4-carboxylic acid [4-(4-[1,2,3]triazol-1-yl-butyl)-phenyl]-amide 11 as a colorless solid. Yield 109 mg (64%); m.p. 183–185° C.

MS: M=482.3 (API+) $^1$H-NMR (400 MHz, CDCl$_3$): 1.65 (m, 2H), 1.95 (m, 2H), 2.65 (t, J=7.5 Hz, 2H), 4.40 (t, J=7.1 Hz, 2H), 7.01 (d, J=16.4 Hz, 1H), 7.16 (d, J=9.5 Hz, 2H), 7.50 (s, 1H), 7.60–7.70 (m, 8H), 8.27 (s, 1H), 8.68 (s, 1H)

Example 12

2-[2-(4-Trifluoromethyl-phenyl)-vinyl]-oxazole-4-carboxylic acid methyl-[4-(4-[1,2,3]triazol-1-yl-butyl)-phenyl]-amide 2-[2-(4-Trifluoromethyl-phenyl)-vinyl]-oxazole-4-carboxylic acid [4-(4-[1,2,3]triazol-1-yl-butyl)-phenyl]-amide (40 mg, 0.083 mmol) is dissolved in acetone (0.6 ml), treated with KOH (17 mg, 0.3 mmol) and iodomethane (17.7 mg, 0.12 mmol) and heated to reflux for 5 min. After cooling the mixture is concentrated, taken up in water (10 ml) and extracted with dichloromethane (2×10 ml). The organic layers are dried over sodium sulfate, concentrated in vacuo and purified by flash column chromatography (ethyl acetate/heptane 9:1) yielding 2-[2-(4-trifluoromethyl-phenyl)-vinyl]-oxazole-4-carboxylic acid methyl-[4-(4-[1,2,3]triazol-1-yl-butyl)-phenyl]-amide 12 as a colorless solid. Yield 30 mg (73%); m.p. 127–129° C.

MS: M=496.3 (API+) $^1$H-NMR (400 MHz, CDCl$_3$): 1.67 (m, 2H), 1.98 (m, 2H), 2.70 (t, J=7.6 Hz, 2H), 3.46 (s, 3H), 4.42 (t, J=6.9 Hz, 2H), 6.69 (br, 1H), 6.90 (d, J=16.4 Hz, 1H), 7.14–7.20 (m, 4H), 7.45–7.63 (m, 6H), 7.71 (s, 1H)

Example 13

[2-(2-Benzo[1,3]dioxol-5-yl-vinyl)-oxazol-4-ylmethyl]-methyl-[4-(4-[1,2,3]triazol-1-yl-butyl)-phenyl]-amine In an analogous manner as described in example 3 but using the corresponding starting materials [2-(2-benzo[1,3]dioxol-5-yl-vinyl)-oxazol-4-ylmethyl]-methyl-[4-(4-[1,2,3]triazol-1-yl-butyl)-phenyl]-amine 13 was obtained as a light yellow solid. Yield 93%

MS: M=458.4 (API+) 1H-NMR(400 MHz, CDCl3): δ=1.60 (m, 2H), 1.93 (m, 2H), 2.56 (t, 2H), 3.01 (s, 3H), 4.38 (t, 2H), 4.41 (s, 2H), 5.99 (s, 2H), 6.71–6.75 (m, 3H), 6.80 (d, 1H), 6.96–7.03 (m, 4H), 7.32 (s, 1H), 7.38 (d, 1H), 7.49 (s, 1H), 7.68 (s, 1H)

Example 14

Methyl-[4-(4-[1,2,3]triazol-1-yl-butyl)-phenyl]-{2-[2-(4-trifluoromethylsulfanyl-phenyl)-vinyl]-oxazol-4-ylmethyl}-amine In an analogous manner as described in example 3 but using the corresponding starting materials methyl-[4-(4-[1,2,3]triazol-1-yl-butyl)-phenyl]-{2-[2-(4-trifluoromethylsulfanyl-phenyl)-vinyl]-oxazol-4-ylmethyl}-amine 14 was obtained as a light yellow solid. Yield 92%

MS: M=514.3 (API+) 1H-NMR(400 MHz, CDCl3): δ=1.60 (m, 2H), 1.93 (m, 2H), 2.56 (t, 2H), 3.02 (s, 3H), 4.38 (t, 2H), 4.43 (s, 2H), 6.72 (d, 2H), 6.94–7.02 (m, 3H), 7.38 (s, 1H), 7.44–7.55 (m, 4H), 7.65–7.68 (m, 3H)

Example 15

{2-[2-(4-Chloro-phenyl)-vinyl]-oxazol-4-ylmethyl}-methyl-[4-(4-[1,2,3]triazol-1-yl-butyl)-phenyl]-amine In an analogous manner as described in example 3 but using the corresponding starting materials {2-[2-(4-chloro-phenyl)-vinyl]-oxazol-4-ylmethyl}-methyl-[4-(4-[1,2,3]triazol-1-yl-butyl)-phenyl]-amine 15 was obtained as a light yellow solid. Yield 78%

MS: M=448.3 (API+) 1H-NMR(400 MHz, CDCl3): δ=1.60 (m, 2H), 1.93 (m, 2H), 2.56 (t, 2H), 3.02 (s, 3H), 4.38 (t, 2H), 4.42 (s, 2H), 6.72 (d, 2H), 6.87 (d, 1H), 7.01 (d, 2H), 7.34–7.44 (m, 6H), 7.48 (s, 1H), 7.68 (s, 1H)

Example 16

[4-(3-[1,2,3]Triazol-1-yl-propoxy)-phenyl]-{2-[2-(4-trifluoromethoxy-phenyl)-vinyl]-oxazol-4-ylmethyl}-amine In an analogous manner as described in example 1 but using the corresponding starting materials [4-(3-[1,2,3]triazol-1-yl-propoxy)-phenyl]-{2-[2-(4-trifluoromethoxy-phenyl)-vinyl]-oxazol-4-ylmethyl}-amine 16 was obtained as a light yellow solid. Yield 8%

MS: M=486.3 (API+) 1H-NMR(400 MHz, CDCl3): δ=2.36 (m, 2H), 3.87 (t, 2H), 3.95 (br, 1H), 4.25 (s, 2H), 4.61 (t, 2H), 6.64 (d, 2H), 6.77 (d, 2H), 6.88 (d, 1H), 7.22–7.26 (m, 3H), 7.46–7.55 (m, 4H), 7.69 (s, 1H)

Example 17

[4-(3-[1,2,3]Triazol-1-yl-propoxy)-phenyl]-{2-[2-(4-trifluoromethylsulfanyl-phenyl)-vinyl]-oxazol-4-ylmethyl}-amine In an analogous manner as described in example 1 but using the corresponding starting materials [4-(3-[1,2,3]triazol-1-yl-propoxy)-phenyl]-{2-[2-(4-trifluoromethylsulfanyl-phenyl)-vinyl]-oxazol-4-ylmethyl}-amine 17 was obtained as a light yellow solid. Yield 24%

MS: M=502.3 (API+) 1H-NMR(400 MHz, CDCl3): δ=2.36 (m, 2H), 3.87 (t, 2H), 3.96 (br, 1H), 4.25 (s, 2H), 4.61 (t, 2H), 6.64 (d, 2H), 6.77 (d, 2H), 6.97 (d, 1H), 7.47–7.56 (m, 5H), 7.65–7.69 (m, 3H)

Example 18

{2-[2-(4-Chloro-phenyl)-vinyl]-oxazol-4-ylmethyl}-[4-(3-[1,2,3]triazol-1-yl-propoxy)-phenyl]-amine In an analogous manner as described in example 1 but using the corresponding starting materials {2-[2-(4-chloro-phenyl)-vinyl]-oxazol-4-ylmethyl}-[4-(3-[1,2,3]triazol-1-yl-propoxy)-phenyl]-amine 18 was obtained as a light yellow solid. Yield 16%

MS: M=436.3 (API+) 1H-NMR(400 MHz, CDCl$_3$): δ=2.36 (m, 2H), 3.87 (t, 2H), 3.96 (br, 1H), 4.24 (s, 2H), 4.61 (t, 2H), 6.64 (d, 2H), 6.77 (d, 2H), 6.87 (d, 1H), 7.35 (d, 2H), 7.43–7.47 (m, 3H), 7.51 (s, 1H), 7.54 (s, 1H), 7.69 (s, 1H)

Example 19

2-[2-(4-Trifluoromethyl-phenyl)-vinyl]-oxazole-4-carboxylic acid [4-(3-[1,2,3]triazol-1-yl-propoxy)-phenyl]-amide In an analogous manner as described in example 11 but using the corresponding starting materials 2-[2-(4-trifluoromethyl-phenyl)-vinyl]-oxazole-4-carboxylic acid [4-(3-[1,2,3]triazol-1-yl-propoxy)-phenyl]-amide 19 was obtained as a light yellow solid. Yield 13%

MS: M=484.2 (API+) 1H-NMR(400 MHz, CDCl$_3$): δ=2.42 (m, 2H), 3.96 (t, 2H), 4.64 (t, 2H), 6.89 (d, 2H), 7.00 (d, 1H), 7.56–7.71 (m, 9H), 8.27 (s, 1H), 8.64 (s, 1H)

Example 20

2-[2-(4-Trifluoromethoxy-phenyl)-vinyl]-oxazole-4-carboxylic acid [4-(3-[1,2,3]triazol-1-yl-propoxy)-phenyl]-amide In an analogous manner as described in example 11 but using the corresponding starting materials 2-[2-(4-Trifluoromethoxy-phenyl)-vinyl]-oxazole-4-carboxylic acid [4-(3-[1,2,3]triazol-1-yl-propoxy)-phenyl]-amide 20 was obtained as a light yellow solid. Yield 99%

MS: M=500.2 (API+) 1H-NMR(400 MHz, [D6]-DMSO): δ=2.28 (m, 2H), 3.95 (t, 2H), 4.57 (t, 2H), 6.91 (d, 2H), 7.23 (d, 1H), 7.44 (d, 2H), 7.67–7.74 (m, 4H), 7.90 (d, 2H), 8.17 (s, 1H), 8.77 (s, 1H), 10.06 (s, 1H)

Example 21

2-[2-(4-Trifluoromethoxy-phenyl)-vinyl]-oxazole-4-carboxylic acid [4-(4-[1,2,3]triazol-1-yl-butyl)-phenyl]-amide In an analogous manner as described in example 11 but using the corresponding starting materials 2-[2-(4-Trifluoromethoxy-phenyl)-vinyl]-oxazole-4-carboxylic acid [4-(4-[1,2,3]triazol-1-yl-butyl)-phenyl]-amide 21 was obtained as a light yellow solid. Yield 57%

MS: M=498.2 (API+) 1H-NMR(400 MHz, CDCl3): δ=1.65 (m, 2H), 1.95 (m, 2H), 2.65 (t, 2H), 4.40 (t, 2H), 6.90 (d, 1H), 7.15 (d, 2H), 7.27 (d, 2H), 7.51 (s, 1H), 7.57–7.62 (m, 5H), 7.70 (s, 1H), 8.25 (s, 1H), 8.69 (s, 1H)

Example 22

2-[2-(4-Trifluoromethoxy-phenyl)-vinyl]-oxazole-4-carboxylic acid methyl-[4-(4-[1,2,3]triazol-1-yl-butyl)-phenyl]-amide In an analogous manner as described in example 12 but using the corresponding starting materials 2-[2-(4-trifluoromethoxy-phenyl)-vinyl]-oxazole-4-carboxylic acid methyl-[4-(4-[1,2,3]triazol-1-yl-butyl)-phenyl]-amide 22 was obtained as a light yellow solid. Yield 55%

MS: M=512.5 (API+) 1H-NMR(400 MHz, CDCl$_3$): δ=1.67 (m, 2H), 1.98 (m, 2H), 2.69 (t, 2H), 3.46 (s, 3H), 4.42 (t, 2H), 6.66 (br, 1H), 6.79 (d, 1H), 7.14–7.22 (m, 6H), 7.43 (d, 1H), 7.48–7.52 (m, 3H), 7.71 (s, 1H)

Example 23

2-[2-(4-Trifluoromethoxy-phenyl)-vinyl]-oxazole-4-carboxylic acid methyl-[4-(3-[1,2,3]triazol-1-yl-propoxy)-phenyl]-amide In an analogous manner as described in example 12 but using the corresponding starting materials 2-[2-(4-trifluoromethoxy-phenyl)-vinyl]-oxazole-4-carboxylic acid methyl-[4-(3-[1,2,3]triazol-1-yl-propoxy)-phenyl]-amide 23 was obtained as a light yellow solid. Yield 45%

MS: M=514.4 (API+) 1H-NMR(400 MHz, CDCl$_3$): δ=2.45 (t, 2H), 3.43 (s, 3H), 3.99 (s, 2H), 4.65 (t, 2H), 6.63 (br, 1H), 6.81 (d, 1H), 6.90 (d, 2H), 7.16 (d, 2H), 7.21 (d, 2H), 7.42–7.50 (m, 3H), 7.58, (s, 1H), 7.72 (s, 1H)

Example 24

{2-[2-(2-Fluoro-4-trifluoromethyl-phenyl)-vinyl]-oxazol-4-ylmethyl}-[4-(4-[1,2,3triazol-1-yl-butyl)-phenyl]-amine In an analogous manner as described in example 1 but using the corresponding starting materials {2-[2-(2-fluoro-4-trifluoromethyl-phenyl)-vinyl]-oxazol-4-ylmethyl}-[4-(4-[1,2,3]triazol-1-yl-butyl)-phenyl]-amine 24 was obtained as a light yellow solid. Yield 6%

MS: M=484.3 (ESI−) 1H-NMR(400 MHz, CDCl$_3$): δ=1.61 (m, 2H), 1.95 (m, 2H), 2.55 (t, 2H), 4.10 (br, 1H), 4.28 (s, 2H), 4.38 (t, 2H), 6.61 (d, 2H), 6.97 (d, 2H), 7.10 (d, 1H), 7.37 (d, 1H), 7.43–7.68 (m, 6H)

Example 25

{2-[2-(3,4-Dichloro-phenyl)-vinyl]-oxazol-4-ylmethyl}-[4-(4-[1,2,3]triazol-1-yl-butyl)-phenyl]-amine In an analogous manner as described in example 1 but using the corresponding starting materials {2-[2-(3,4-dichloro-phenyl)-vinyl]-oxazol-4-ylmethyl}-[4-(4-[1,2,3]triazol-1-yl-butyl)-phenyl]-amine 25 was obtained as a light yellow solid. Yield 13%;

m.p.76.8–78.8° C. MS: M=468.3 (API+) 1H-NMR(400 MHz, CDCl3): δ=1.59 (m,2H), 1.93 (m, 2H), 2.55 (t, 2H), 4.08 (br, 1H), 4.27 (s, 2H), 4.38 (t, 2H), 6.61 (d, 2H), 6.88 (d, 1H), 6.96 (d, 2H), 7.33–7.52 (m, 5H), 7.59 (s, 1H), 7.69 (s, 1H)

Example 26

[4-(4-[1,2,3]Triazol-1-yl-butyl)-phenyl]-{2-[2-(3-trifluoromethyl-phenyl)-vinyl]-oxazol-4-ylmethyl}-amine In an analogous manner as described in example 1 but using the corresponding starting materials [4-(4-[1,2,3]triazol-1-yl-butyl)-phenyl]-{2-[2-(3-trifluoromethyl-phenyl)-vinyl]-oxazol-4-ylmethyl}-amine 26 was obtained as a light yellow solid. Yield 19%

MS: M=468.4 (API+) 1H-NMR(400 MHz, CDCl$_3$): δ=1.59 (m, 2H), 1.93 (m, 2H), 2.55 (t, 2H), 4.28 (s, 2H), 4.38 (t, 2H), 6.61 (d,2H), 6.95–6.99 (m, 3H), 7.48–7.60 (m, 5H), 7.69 (d, 2H), 7.75 (s, 1H)

Example 27

{2-[2-(4-Fluoro-2-trifluoromethyl-phenyl)-vinyl]-oxazol-4-ylmethyl}-[4-(4-[1,2,3]triazol-1-yl-butyl)-phenyl]-amine In an analogous manner as described in example 1 but using the corresponding starting materials {2-[2-(4-fluoro-2-trifluoromethyl-phenyl)-vinyl]-oxazol-4-ylmethyl}-[4-(4-[1,2,3]triazol-1-yl-butyl)-phenyl]-amine 27 was obtained as a light yellow solid. Yield 21%; m.p. 109–111° C.

MS: M=486.3 (API+) 1H-NMR(400 MHz, CDCl$_3$): δ=1.61 (m, 2H), 1.90 (m, 2H), 2.55 (t, 2H), 4.28 (t, 2H), 6.61 (d, 2H), 6.84 (d, 1H), 6.97 (d, 2H), 7.28 (m, 1H), 7.41 (d, 1H), 7.51 (d, 2H), 7.68–7.78 (m, 3H)

Example 28

[4-(4-[1,2,3]Triazol-1-yl-butyl)-phenyl]-{2-[2-(3-trifluoromethoxy-phenyl)-vinyl]-oxazol-4-ylmethyl}-amine In an analogous manner as described in example 1 but using the corresponding starting materials [4-(4-[1,2,3]Triazol-1-yl-butyl)-phenyl]-{2-[2-(3-trifluoromethoxy-phenyl)-vinyl]-oxazol-4-ylmethyl}-amine 28 was obtained as a light yellow solid. Yield 19%;

m.p. 91–93° C. MS: M=484.4 (API+) 1H-NMR(400 MHz, CDCl$_3$): δ=1.61 (m,2H), 1.93 (m, 2H), 2.55 (t,2H), 4.10 (br, 1H), 4.27 (s, 2H), 4.38 (t, 2H), 6.61 (d, 2H), 6.90–6.98 (m, 3H), 7.19 (d, 1H), 7.35 (s, 1H), 7.39–7.52 (m, 5H), 7.68 (s, 1H)

Example 29

2-[2-(2,2-Difluoro-benzo [1,3]dioxol-5-yl)-vinyl]-oxazole-4-carboxylic acid [4-(4-[1,2,3]triazol-1-yl-butyl)-phenyl]-amide In an analogous manner as described in example 11 but using the corresponding starting materials 2-[2-(2,2-difluoro-benzo [1,3]dioxol-5-yl)-vinyl]-oxazole-4-carboxylic acid [4-(4-[1,2,3]triazol-1-yl-butyl)-phenyl]-amide 29 was obtained as a light yellow solid.

Yield 10% MS: M=493.06(ESI) 1H-NMR(300 MHz, CDCl$_3$): δ=1.68(m, 2H), 2.06(m, 2H), 2.65(m, 2H), 4.43(t, 2H 6.89(d, 1H), 7.10–7.20(m, 3H), 7.30(m, 2H), 7.60–7.80 (m, 4H), 7.80(s, 1H), 8.30(s, 1H), 8.72(s, 1H).

Example 30

2-[2-(2,2-Difluoro-benzo [1,3]dioxol-5-yl)-vinyl]-oxazole-4-carboxylic acid methyl-[4-(4-1,2,3]-triazol-1-yl-butyl)-phenyl]-amide In an analogous manner as described in example 12 but using the corresponding starting materials 2-[2-(2,2-Difluoro-benzo[1,3]dioxol-5-yl)-vinyl]-oxazole-4-carboxylic acid methyl-[4-(4-[1,2,3]triazol-1-yl-butyl)-phenyl]-amide 30 was obtained as a light yellow solid. Yield 61% MS: M=507.2 (ESI) 1H-NMR (300 MHz, CDCl$_3$): δ=1.68(m, 2H), 2.02(m, 2H), 2.72(t, 2H), 3.47(s, 3H), 4.42(t, 2H), 6.30–7.75 (m, 12H).

Example 31

2-[2-(4-Difluoromethoxy-phenyl)-vinyl]-oxazole-4-carboxylic acid-[4-(4-[1,2,3]triazol-1-yl-butyl)-phenyl]-amide In an analogous manner as described in example 11 but using the corresponding starting materials 2-[2-(4-difluoromethoxy-phenyl)-vinyl]-oxazole-4-carboxylic acid-[4-(4-[1,2,3]triazol-1-yl-butyl)-phenyl]-amide 31 was obtained as a light yellow solid. Yield 3%

MS: M=479.2 (ESI) 1H-NMR (300 MHz, CDCl$_3$): δ=1.72(m, 2H), 1.99(m, 2H), 2.69(t, 2H), 4.42(t, 2H), 6.3–8.8 ppm (m,13H).

Example 32

2-[2-(4-Difluoromethoxy-phenyl)-vinyl]-oxazole-4-carboxylic acid methyl-[4-(4-[1,2,3]-triazol-1-yl-butyl)-phenyl]-amide In an analogous manner as described in example 12 but using the corresponding starting materials 2-[2-(4-Difluoromethoxy-phenyl)-vinyl]-oxazole-4-carboxylic acid methyl-[4-(4-[1,2,3]triazol-1-yl-butyl)-phenyl]-amide 32 was obtained as a light yellow solid. Yield 42%

MS: M=493.3 (ESI) 1H-NMR (300 MHz, CDCl$_3$): δ=1.68(m, 2H), 1.99(m, 2H), 2.69(t, 2H), 3.46 (s, 3H), 4.42(t, 2H), 6.3–8.8 ppm (aromatic, vinyl, 13H)

Example 33

[4-(4-[1,2,3]Triazol-1-yl-butyl)phenyl]-{2-[(E)-2-(-4-trifluoromethanesulfinyl-phenyl)-vinyl]-oxazol-4-ylmethyl}-amine To an ice-cold solution of [4-(4-[1,2,3]triazol-1-yl-butyl) phenyl]-carbamic acid tert-butyl ester (188 mg, 0.6 mmol) in N,N-dimethylformamide (5 ml) was added sodium hydride (16.5 mg, 0.65 mmol) and the mixture stirred for 30 min. After addition of 4-chloromethyl-2-[2-(4-trifluoromethanesulfinyl-phenyl)-vinyl]-oxazole (200 mg, 0.6 mmol), the mixture was stirred at room temperature over night, then mixed with 40 ml ammonium chloride solution, thoroughly extracted with ethyl acetate and the extract dried and evaporated. Flash column chromatography (ethyl acetate/heptane 2:1) yielded 105 mg (29%) [4-(4-[1,2,3]triazol-1-yl-butyl) phenyl]-{2-[(E)-2-(–4-trifluoromethanesulfinyl-phenyl)-vinyl]-oxazol-4-ylmethyl}-carbamic acid tert-butyl ester as oily residue.

MS: M=616.2 (API+) 1H-NMR(400 MHz, CDCl$_3$): δ=1.44 (s, 9H), 1.65 (m, 2H), 1.93 (m, 2H), 2.63 (t, 2H), 4.39 (t, 2H), 4.73 (s, 2H), 7.04 (d, 1H), 7.09 (d, 2H), 7.21 (d, 2H), 7.48 (s, 2H), 7.54 (d, 1H), 7.69 (s, 1H), 7.73 (d, 2H), 7.81 (d, 2H).

A solution of [4-(4-[1,2,3]triazol-1-yl-butyl)phenyl]-{2-[(E)-2-(–4-trifluoro-methanesulfinyl-phenyl)-vinyl]-oxazol-4-ylmethyl}-carbamic acid tert-butyl ester (100 mg, 0.16 mmol) in dichloromethane (3 ml) and trifluoroacetic acid (3 ml) was stirred at room temperature for 1 h. The mixture was quenched with water, neutralized with sodium carbonate and the organic phase separated, dried and evaporated. Crystallization from ether yielded 82 mg (98%) of [4-(4-[1,2,3]Triazol-1-yl-butyl)phenyl]-{2-[(E)-2-(–4-trifluoromethanesulfinyl-phenyl)-vinyl]-oxazol-4-ylmethyl}-amine 33 as off-white solid melting at 121–124° C.

MS: M=516.1 (API+) 1H-NMR(400 MHz, CDCl$_3$): δ=1.60 (m, 2H), 1.93 (m, 2H), 2.55 (t, 2H), 4.29 (s, 2H), 4.39 (t, 2H), 6.62 (d, 2H), 6.97 (d, 2H), 7.04 (d, 1H), 7.49 (s, 1H), 7.53 (d, 1H), 7.55 (s, 1H), 7.69 (s, 1H), 7.73 (d, 2H), 7.81 (d, 2H)

Example 34

{2-[2-(2,4-Difluoro-phenyl)-vinyl]-oxazol-4-ylmethyl}-[4-(4-[1,2,3]triazol-1-yl-butyl)-phenyl]-amine In an analogous manner as described in example 33 but using the corresponding starting materials {2-[2-(2,4-difluoro-phenyl)-vinyl]-oxazol-4-ylmethyl}-[4-(4-[1,2,3]triazol-1-yl-butyl)-phenyl]-carbamic acid tert-butyl ester was obtained as a light yellow solid. Yield 66%

MS: M=536.3 (API+) 1H-NMR(400 MHz, CDCl$_3$): δ=1.44 (s, 9H), 1.64 (m, 2H), 1.94 (m, 2H), 2.62 (t, 2H), 4.38 (t, 2H), 4.73 (s, 2H), 6.86–6.97 (m, 3H), 7.08 (m, 2H), 7.21 (d, 2H), 7.48–7.54 (m, 4H), 7.69 (s, 1H)

In an analogous manner as described in example 33 but using the corresponding starting materials {2-[2-(2,4-difluoro-phenyl)-vinyl]-oxazol-4-ylmethyl}-[4-(4-[1,2,3]triazol-1-yl-butyl)-phenyl]-amine 34 was obtained as a light yellow solid. Yield 98%

MS: M=436.3 (API+) 1H-NMR(400 MHz, CDCl$_3$): δ=1.60 (m, 2H), 1.93 (m, 2H), 2.55 (t, 2H), 4.09 (br, 1H), 4.27 (s, 2H), 4.38 (t, 2H), 6.61 (d, 2H), 6.84–6.98 (m, 5H), 7.48–7.57 (m, 4H), 7.68 (s, 1H)

Example 35

{2-[2-(4-Chloro-2-fluoro-phenyl)-vinyl]-oxazol-4-ylmethyl}-[4-(4-[1,2,3]triazol-1-yl-butyl)-phenyl]-amine In an analogous manner as described in example 33 but using the corresponding starting materials {2-[2-(4-chloro-2-fluoro-phenyl)-vinyl]-oxazol-4-ylmethyl}-[4-(4-[1,2,3] triazol-1-yl-butyl)-phenyl]-carbamic acid tert-butyl ester was obtained as a light yellow solid. Yield 82%

MS: M=552.3 (API+) 1H-NMR(400 MHz, CDCl₃): δ=1.44 (s, 9H), 1.63 (m, 2H), 1.94 (m, 2H), 2.62 (t, 2H), 4.38 (t, 2H), 4.72 (s, 2H), 6.99 (d, 1H), 7.07–7.22 (m, 6H), 7.46–7.54 (m, 4H), 7.69 (s, 1H)

In an analogous manner as described in example 33 but using the corresponding starting materials {2-[2-(4-chloro-2-fluoro-phenyl)-vinyl]-oxazol-4-ylmethyl}-[4-(4-[1,2,3]triazol-1-yl-butyl)-phenyl]-amine 35 was obtained as a light yellow solid. Yield 77%

MS: M=452.3 (API+) 1H-NMR(400 MHz, CDCl₃): δ=6=1.60 (m, 2H), 1.93 (m, 2H), 2.55 (t, 2H), 4.09 (br, 1H), 4.27 (s, 2H), 4.37 (t, 2H), 6.97 (d, 2H), 7.01 (s, 1H), 7.12–7.17 (m, 2H), 7.45–7.57 (m, 4H), 7.68 (s, 1H)

Example 36

[4-(2-[1,2,3]Triazol-1-yl-ethoxymethyl)-phenyl]-{2-[2-(4-trifluoromethoxy-phenyl)-vinyl]-oxazol-4-ylmethyl}-amine In an analogous manner as described in example 1 but using the corresponding starting materials [4-(2-[1,2,3]triazol-1-yl-ethoxymethyl)-phenyl]-{2-[2-(4-trifluoromethoxy-phenyl)-vinyl]-oxazol-4-ylmethyl}-amine 36 was obtained as a light yellow solid. Yield 15%

MS: M=486.2 (API+) 1H-NMR(400 MHz, CDCl₃): δ=3.80 (t, 2H), 4.29 (s, 2H), 4.38 (s, 2H), 4.56 (t, 2H), 6.24 (d, 2H), 6.88 (d, 1H), 7.08 (d, 2H), 7.23 (d, 2H), 7.46–7.55 (m, 4H), 7.68 (s, 2H)

Example 37

[4-(2-[1,2,3]Triazol-1-yl-ethoxymethyl)-phenyl]-{2-[2-(4-trifluoromethyl-phenyl)-vinyl]-oxazol-4-ylmethyl}-amine In an analogous manner as described in example 1 but using the corresponding starting materials [4-(2-[1,2,3]triazol-1-yl-ethoxymethyl)-phenyl]-{2-[2-(4-trifluoromethyl-phenyl)-vinyl]-oxazol-4-ylmethyl}-amine 37 was obtained as a light yellow solid. Yield 12%

MS: M=357.2 (API+) 1H-NMR(400 MHz, CDCl₃): δ=3.80 (t, 2H), 4.30 (s, 2H), 4.38 (s, 2H), 4.56 (t, 2H), 6.24 (d, 2H), 6.98 (d, 1H), 7.08 (d, 2H), 7.52 (d, 2H), 7.60–7.66 (m, 4H), 7.69 (s, 2H)

Example 38

[4-(4-[1,2,3]Triazol-1-yl-but-1-enyl)-phenyl]-{2-[2-(4-trifluoromethanesulfinyl-phenyl)-vinyl]-oxazol-4-ylmethyl}-amine A solution of [4-(4-[1,2,3]triazol-1-yl-but-1-enyl)-phenyl]-carbamic acid tert-butyl ester (0.157 g, 0.5 mmol) in N,N-dimethyl formamide (4 ml) was treated with sodium hydride (0.014 g, 0.5 mmol) and stirred for 30 min at room temperature. After addition of 4-chloromethyl-2-[2-(4-trifluoromethanesulfinyl-phenyl)-vinyl]-oxazole (0.168 g, 0.5 mmol) and stirring for 12 h the reaction was quenched by the addition of a sat. NH₄Cl solution (8 ml). Extraction with ethyl acetate (3×10 ml), washing with water, drying over sodium sulfate and concentration in vacuo yields crude [4-(4-[1,2,3]triazol-1-yl-but-1-enyl)-phenyl]-{2-[2-(4-trifluoromethane-sulfinyl-phenyl)-vinyl]-oxazol-4-ylmethyl}-carbamic acid tert-butyl ester (0.28 g) which was used in the next step without any further purification.

The crude carbamic ester was stirred in a mixture of trifluoroacetic acid/dichloro methane (1:1, 28 ml) for 2 h. Water (50 ml) was added and the solution was neutralized by careful addition of sodium carbonate. The organic layer is separated, washed with water and concentrated. Purification was achieved by flash column chromatography (ethyl acetate/heptane 4:1) and washing with methanol yielding [4-(4-[1,2,3]triazol-1-yl-but-1-enyl)-phenyl]-{2-[2-(4-trifluoromethanesulfinyl-phenyl)-vinyl]-oxazol-4-ylmethyl}-amine 38 (25 mg, 10%) as a yellow solid.

MS: M=514.0 (ESI+)

What is claimed is:

1. A compound of formula (I)

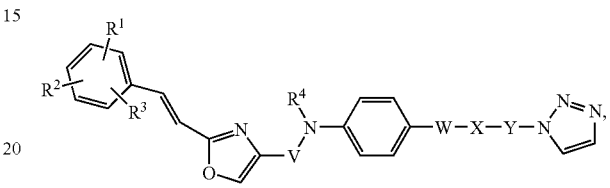

formula (I)

wherein
R¹ is halogen;
—O-alkyl;
—S-alkyl; —S(O)-alkyl; —S(O)₂-alkyl;
—N-alkyl; or
alkyl, wherein each of the alkyl groups are independently unsubstituted or substituted once or several times with halogen; and
R² is hydrogen; or
halogen; or alternatively
R¹ and R² together with the carbon atoms to which they are attached form a 5 or 6 membered heterocyclic ring; and
R³ is hydrogen; or
halogen, provided that when R¹ and R² together with the carbon atoms to which they are attached do not form a 5 or 6 member heterocyclic ring, R³ is hydrogen;
R⁴ is hydrogen; or
alkyl;
V is —CH₂—; or
—C(O)—;
W is —CH₂—; or
a direct bond;
X is —NH—, —O—, —S—, —S(O)—, —S(O)₂—, —C(O)—, —C(O)NH—, —NHC(O)—, —S(O)₂NH—, —CH═CH—, or —CH₂—;
Y is —(CH₂)ₙ—; and
n is 1, 2 or 3;
or their pharmaceutically acceptable salts.

2. The compound according to claim 1, wherein
R¹ is halogen;
—O-alkyl;
—S-alkyl; or
alkyl, wherein each of the alkyl groups are independently unsubstituted or substituted once or several times with halogen; and
R², R³ are both hydrogen; and
R⁴ is hydrogen; or
methyl;
V is —CH₂—; and
—W—X—Y— is —(CH₂)₄—;
or their pharmaceutically acceptable salts.

3. The compound according to claim 2, wherein the compound is selected from the group consisting of
[4-(4-[1,2,3]Triazol-1-yl-butyl)-phenyl]-{2-[2-(4-trifluoromethoxy-phenyl)-vinyl]-oxazol-4-ylmethyl}-amine;
[4-(4-[1,2,3]Triazol-1-yl-butyl)-phenyl]-{2-[2-(4-trifluoromethyl-phenyl)-vinyl]-oxazol-4-ylmethyl}-amine;
Methyl-[4-(4-[1,2,3]triazol-1-yl-butyl)-phenyl]-{2-[2-(4-trifluoromethyl-phenyl)-vinyl]-oxazol-4-ylmethyl}-amine;
{2-[2-(4-Difluoromethoxy-phenyl)-vinyl]-oxazol-4-ylmethyl}-[4-(4-[1,2,3]triazol-1-yl-butyl)-phenyl]-amine;
{2-[2-(4-Chloro-phenyl)-vinyl]-oxazol-4-ylmethyl}-[4-(4-[1,2,3]triazol-1-yl-butyl)-phenyl]-amine;
[4-(4-[1,2,3]Triazol-1-yl-butyl)-phenyl]-{2-[2-(4-trifluoromethylsulfanyl-phenyl)-vinyl]-oxazol-4-ylmethyl}-amine;
Methyl-[4-(4-[1,2,3]triazol-1-yl-butyl)-phenyl]-{2-[2-(4-trifluoromethylsulfanyl-phenyl)-vinyl]-oxazol-4-ylmethyl}-amine;
{2-[2-(4-Chloro-phenyl)-vinyl]-oxazol-4-ylmethyl}-methyl-[4-(4-[1,2,3]triazol-1-yl-butyl)-phenyl]-amine;
[4-(4-[1,2,3]Triazol-1-yl-butyl)-phenyl]-{2-[2-(3-trifluoromethyl-phenyl)-vinyl]-oxazol-4-ylmethyl}-amine; and
[4-(4-[1,2,3]Triazol-1-yl-butyl)-phenyl]-{2-[2-(3-trifluoromethoxy-phenyl)-vinyl]-oxazol-4-ylmethyl}-amine.

4. The compound according to claim 1, wherein
$R^1$ is halogen;
—O-alkyl; or
alkyl, wherein each of the alkyl groups are independently unsubstituted or substituted once or several times with halogen; and
$R^2$ is halogen;
$R^3$ is hydrogen; and
$R^4$ is hydrogen; or
methyl;
V is —CH$_2$—; and
—W—X—Y— is —(CH$_2$)$_4$—;
or their pharmaceutically acceptable salts.

5. The compound according to claim 4, wherein the compound is selected from the group consisting of
{2-[2-(2-Fluoro-4-trifluoromethyl-phenyl)-vinyl]-oxazol-4-ylmethyl}-[4-(4-[1,2,3]triazol-1-yl-butyl)-phenyl]-amine;
{2-[2-(3,4-Dichloro-phenyl)-vinyl]-oxazol-4-ylmethyl}-[4-(4-[1,2,3]triazol-1-yl-butyl)-phenyl]-amine;
{2-[2-(4-Fluoro-2-trifluoromethyl-phenyl)-vinyl]-oxazol-4-ylmethyl}-[4-(4-[1,2,3]triazol-1-yl-butyl)-phenyl]-amine;
{2-[(E)-2-(2,4-Difluoro-phenyl)-vinyl]-oxazol-4-ylmethyl}-[4-(4-[1,2,3]triazol-1-yl-butyl)-phenyl]-amine; and
{2-[(E)-2-(4-Chloro-2-fluoro-phenyl)-vinyl]-oxazol-4-ylmethyl}-[4-(4-[1,2,3]triazol-1-yl-butyl)-phenyl]-amine.

6. The compound according to claim 1, wherein
$R^1$ and $R^2$ together with the carbon atoms to which they are attached form a 5 or 6 membered heterocyclic ring; and
$R^3$ is hydrogen; or
halogen;
$R^4$ is hydrogen; or
methyl;
V is —CH$_2$—; and
—W—X—Y— is —(CH$_2$)$_4$—;
or their pharmaceutically acceptable salts.

7. The compound according to claim 6, wherein the compound is selected from the group consisting of
[2-(2-Benzo[1,3]dioxol-5-yl-vinyl)-oxazol-4-ylmethyl]-[4-(4-[1,2,3]triazol-1-yl-butyl)-phenyl]-amine;
{2-[2-(2,2-Difluoro-benzo[1,3]dioxol-5-yl)-vinyl]-oxazol-4-ylmethyl}-[4-(4-triazol-1-yl-butyl)-phenyl]-amine; and
[2-(2-Benzo[1,3]dioxol-5-yl-vinyl)-oxazol-4-ylmethyl]-methyl-[4-(4-[1,2,3]triazol-1-yl-butyl)-phenyl]-amine.

8. The compound according to claim 1, wherein
$R^1$ is halogen;
—O-alkyl;
—S-alkyl; or
alkyl, wherein each of the alkyl groups are independently unsubstituted or substituted once or several times with halogen; and
$R^2$, $R^3$ are both hydrogen; and
$R^4$ is hydrogen; or
methyl;
V is —C(O)—; and
—W—X—Y— is —(CH$_2$)$_4$—;
or their pharmaceutically acceptable salts.

9. The compound according to claim 8, wherein the compound is selected from the group consisting of
2-[2-(4-Trifluoromethyl-phenyl)-vinyl]-oxazole-4-carboxylic acid [4-(4-[1,2,3]triazol-1-yl-butyl)-phenyl]-amide;
2-[2-(4-Trifluoromethyl-phenyl)-vinyl]-oxazole-4-carboxylic acid methyl-[4-(4-[1,2,3]triazol-1-yl-butyl)-phenyl]-amide;
2-[2-(4-Trifluoromethoxy-phenyl)-vinyl]-oxazole-4-carboxylic acid [4-(4-[1,2,3]triazol-1-yl-butyl)-phenyl]-amide;
2-[2-(4-Trifluoromethoxy-phenyl)-vinyl]-oxazole-4-carboxylic acid methyl-[4-(4-[1,2,3]triazol-1-yl-butyl)-phenyl]-amide;
2-[(E)-2-(4-Difluoromethoxy-phenyl)-vinyl]-oxazole-4-carboxylic acid [4-(4-[1,2,3]triazol-1-yl-butyl)-phenyl]-amide; and
2-[(E)-2-(4-Difluoromethoxy-phenyl)-vinyl]-oxazole-4-carboxylic acid methyl-[4-(4-[1,2,3]triazol-1-yl-butyl)-phenyl]-amide.

10. The compound according to claim 1, wherein
$R^1$ is halogen;
—O-alkyl; or
alkyl, wherein each of the alkyl groups are independently unsubstituted or substituted once or several times with halogen; and
$R^2$ is halogen;
$R^3$ is hydrogen; and
$R^4$ is hydrogen; or
methyl;
V is —C(O)—; and
—W—X—Y— is —(CH$_2$)$_4$—;
or their pharmaceutically acceptable salts.

11. The compound according to claim 1, wherein
$R^1$ and $R^2$ together with the carbon atoms to which they are attached form a 5 or 6 membered heterocyclic ring; and
$R^3$ is hydrogen; or
halogen;
$R^4$ is hydrogen; or
methyl;
V is —C(O)—; and
—W—X—Y— is —(CH$_2$)$_4$—;
or their pharmaceutically acceptable salts.

12. The compound according to claim 11, wherein the compound is selected from the group consisting of
2-[(E)-2-(2,2-Difluoro-benzo[1,3]dioxol-5-yl)-vinyl]-oxazole-4-carboxylic acid methyl-[4-(4-[1,2,3]triazol-1-yl-butyl)-phenyl]-amide; and
2-[(E)-2-(2,2-Difluoro-benzo[1,3]dioxol-5-yl)-vinyl]-oxazole-4-carboxylic acid [4-(4-[1,2,3]triazol-1-yl-butyl)-phenyl]-amide.

13. The compound according to claim 1, wherein
$R^1$ is halogen;
—O-alkyl;
—S-alkyl; —S(O)-alkyl; —S(O)$_2$-alkyl
—N-alkyl; or
alkyl, wherein each of the alkyl groups are independently unsubstituted or substituted once or several times with halogen; and
$R^2$ is hydrogen; or
halogen; and
$R^3$ is hydrogen;
$R^4$ is hydrogen; or
methyl; and
V is —CH$_2$—; or
—C(O)—; and
—W—X—Y— is —O—(CH$_2$)$_3$—; —C(O)—(CH$_2$)$_3$—; —S—(CH$_2$)$_3$—; —S(O)$_2$—(CH$_2$)$_3$—; —S(O)—(CH$_2$)$_3$—; —S(O)$_2$—NH—(CH$_2$)$_2$—; —NH—C(O)—(CH$_2$)$_2$—; —C(O)—NH—(CH$_2$)$_2$—; —CH$_2$—NH—(CH$_2$)$_2$—; —CH=CH—(CH$_2$)$_2$— or —CH$_2$—CH=CH—CH$_2$—;
or their pharmaceutically acceptable salts.

14. The compound according to claim 13, wherein the compound is selected from the group consisting of
[4-(3-[1,2,3]Triazol-1-yl-propoxy)-phenyl]-{2-[2-(4-trifluoromethyl-phenyl)-vinyl]-oxazol-4-ylmethyl}-amine;
Methyl-[4-(3-[1,2,3]triazol-1-yl-propoxy)-phenyl]-{2-[2-(4-trifluoromethyl-phenyl)-vinyl]-oxazol-4-ylmethyl}-amine;
[4-(3-[1,2,3]Triazol-1-yl-propoxy)-phenyl]-{2-[2-(4-trifluoromethoxy-phenyl)-vinyl]-oxazol-4-ylmethyl}-amine;
[4-(3-[1,2,3]Triazol-1-yl-propoxy)-phenyl]-{2-[2-(4-trifluoromethylsulfanyl-phenyl)-vinyl]-oxazol-4-ylmethyl}-amine;
{2-[2-(4-Chloro-phenyl)-vinyl]-oxazol-4-ylmethyl}-[4-(3-[1,2,3]triazol-1-yl-propoxy)-phenyl]-amine;
2-[2-(4-Trifluoromethyl-phenyl)-vinyl]-oxazole-4-carboxylic acid [4-(3-[1,2,3]triazol-1-yl-propoxy)-phenyl]-amide;
2-[2-(4-Trifluoromethoxy-phenyl)-vinyl]-oxazole-4-carboxylic acid [4-(3-[1,2,3]triazol-1-yl-propoxy)-phenyl]-amide;
2-[2-(4-Trifluoromethoxy-phenyl)-vinyl]-oxazole-4-carboxylic acid methyl-[4-(3-[1,2,3]triazol-1-yl-propoxy)-phenyl]-amide; and
[4-(4-[1,2,3]Triazol-1-yl-but-1-enyl)-phenyl]-{2-[2-(4-trifluoromethanesulfinyl-phenyl)-vinyl]-oxazol-4-ylmethyl}-amine.

15. The compound according to claim 1, wherein
$R^1$ and $R^2$ together with the carbon atoms to which they are attached form a 5 or 6 membered heterocyclic ring; and
$R^3$ is hydrogen; or
halogen;
$R^4$ is hydrogen; or
methyl;
V is —CH$_2$—; or
—C(O)—; and
—W—X—Y— is —O—(CH$_2$)$_3$—; —C(O)—(CH$_2$)$_3$—; —S—(CH$_2$)$_3$—; —S(O)$_2$—(CH$_2$)$_3$—; —S(O)—(CH$_2$)$_3$—; —S(O)$_2$—NH—(CH$_2$)$_2$—; —NH—C(O)—(CH$_2$)$_2$—; —C(O)—NH—(CH$_2$)$_2$—; —CH$_2$—NH—(CH$_2$)$_2$—; —CH=CH—(CH$_2$)$_2$— or —CH$_2$—CH=CH—CH$_2$—;
or their pharmaceutically acceptable salts.

16. The compound according to claim 15, where in the compound is selected from the group consisting of
[4-(2-[1,2,3]Triazol-1-yl-ethoxymethyl)-phenyl]-{2-[2-(4-trifluoromethoxy-phenyl)-vinyl]-oxazol-4-ylmethyl}-amine;
[4-(2-[1,2,3]Triazol-1-yl-ethoxymethyl)-phenyl]-{2-[2-(4-trifluoromethyl-phenyl)-vinyl]-oxazol-4-ylmethyl}-amine; and
[4-(4-[1,2,3]Triazol-1-yl-butyl)-phenyl]-{2-[(E)-2-(4-trifluoromethanesulfinyl-phenyl ]-oxazol-4-ylmethyl}-amine.

17. A process for the manufacture of the compounds of formula (I) of claim 1, comprising:
reacting a compound of formula (VI)

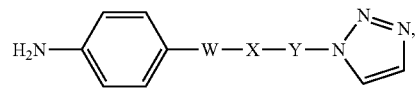
(formula VI)

with a compound of formula (VII)

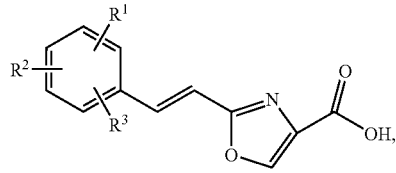
(formula VII)

to give a compound of formula (I) wherein V is —C(O)— and $R^4$ is hydrogen.

18. The process according to claim 17, further comprising reacting the compound of formula VII with an alkyl halide to give the corresponding compound of formula (I) wherein $R^4$ is alkyl.

19. The process according to claim 17, further comprising isloating the compound of formula (I).

20. The process according to claim 17, further comprising forming a pharmaceutically acceptable salt of the compound of formula (I).

21. A process for the manufacture of the compounds of formula (I) of claim 1, comprising:
reacting a compound of formula (VI)

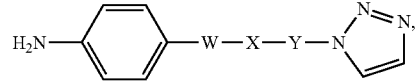
(formula VI)

with a compound of formula (V),

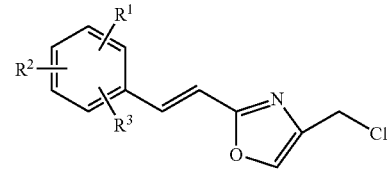
formula (V)

to give a compound of formula (I) wherein V is —CH$_2$— and R$^4$ is hydrogen.

22. The process according to claim 21, further comprising reacting the compound of formula VII with an aldehyde to give the corresponding compound of formula (I) wherein R$^4$ is alkyl.

23. The process according to claim 21, further comprising isloating the compound of formula (I).

24. The process according to claim 21, further comprising forming a pharmaceutically acceptable salt of the compound of formula (I).

25. A pharmaceutical composition comprising a compound of formula (I)

formula (I)

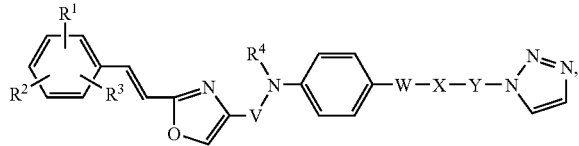

wherein
R$^1$ is halogen;
—O-alkyl;
—S-alkyl; —S(O)-alkyl; —S(O)$_2$-alkyl;
—N-alkyl; or
alkyl, wherein each of the alkyl groups are independently unsubstituted or substituted once or several times with halogen; and R$^2$ is hydrogen; or
halogen; or alternatively R$^1$ and R$^2$ together with the carbon atoms to which they are attached form a 5 or 6 membered heterocyclic ring; and R$^3$ is hydrogen; or
halogen, provided that when R$^1$ and R$^2$ together with the carbon atoms to which they are attached do not form a 5 or 6 member heterocyclic ring, R$^3$ is hydrogen;

R$^4$ is hydrogen; or
alkyl;

V is —CH$_2$—; or
—C(O)—;

W is —CH$_2$—; or
a direct bond;

X is —NH—, —O—, —S—, —S(O)—, —S(O)$_2$—, —C(O)—, —C(O)NH—, —NHC(O)—, —S(O)$_2$NH—, —CH=CH—, or —CH$_2$—;

Y is —(CH$_2$)$_n$—; and n is 1, 2 or 3;

or their pharmaceutically acceptable salts;
and a pharmaceutically acceptable carrier.

* * * * *